United States Patent
Gilheany et al.

(10) Patent No.: US 10,196,338 B2
(45) Date of Patent: Feb. 5, 2019

(54) CHIRAL DIAMINE COMPOUNDS FOR THE PREPARATION OF CHIRAL ALCOHOLS AND CHIRAL AMINES

(71) Applicant: University College Dublin, Dublin (IE)

(72) Inventors: Declan Gilheany, Dublin (IE); Bartosz Bieszczad, Dublin (IE)

(73) Assignee: UNIVERSITY COLLEGE DUBLIN, Dublin (IE)

( * ) Notice: Subject to any disclaimer, the term of this patent is extended or adjusted under 35 U.S.C. 154(b) by 0 days.

(21) Appl. No.: 15/313,474

(22) PCT Filed: May 26, 2015

(86) PCT No.: PCT/EP2015/061610
§ 371 (c)(1),
(2) Date: Nov. 22, 2016

(87) PCT Pub. No.: WO2015/181182
PCT Pub. Date: Dec. 3, 2015

(65) Prior Publication Data
US 2017/0204036 A1 Jul. 20, 2017

(30) Foreign Application Priority Data

May 26, 2014 (GB) .................................. 1409317.3

(51) Int. Cl.
| | | |
|---|---|---|
| C07C 45/69 | (2006.01) | |
| C07C 29/40 | (2006.01) | |
| C07D 311/76 | (2006.01) | |
| C07D 235/12 | (2006.01) | |
| C07C 211/36 | (2006.01) | |
| C07C 211/53 | (2006.01) | |
| C07C 215/50 | (2006.01) | |
| C07C 215/64 | (2006.01) | |
| C07C 41/30 | (2006.01) | |

(52) U.S. Cl.
CPC .............. *C07C 45/69* (2013.01); *C07C 29/40* (2013.01); *C07C 41/30* (2013.01); *C07C 211/36* (2013.01); *C07C 211/53* (2013.01); *C07C 215/50* (2013.01); *C07C 215/64* (2013.01); *C07D 235/12* (2013.01); *C07D 311/76* (2013.01); *C07B 2200/07* (2013.01); *C07C 2601/08* (2017.05); *C07C 2601/14* (2017.05); *C07C 2601/16* (2017.05); *C07C 2602/08* (2017.05); *C07C 2602/10* (2017.05); *C07C 2602/18* (2017.05)

(58) Field of Classification Search
None
See application file for complete search history.

(56) References Cited

U.S. PATENT DOCUMENTS 4,165,330 A    8/1979  Whitney et al.
2004/0249184 A1 12/2004  Beller et al.

FOREIGN PATENT DOCUMENTS

| CN | 101844958 A | 9/2010 |
| DE | 10150335 A1 | 4/2003 |
| WO | 9950205 A2 | 10/1999 |

OTHER PUBLICATIONS

International Search Report and Written Opinion issued in PCT/EP2015/061610 dated Sep. 2, 2015.
Guido Zadel et al: "(5aS, 10aS)-Octahydro-1 H,5H-dipyrrolo [1,2-a:1',2Prime;-d]pyrazin DPPals Hilfsreagenz bei der enantioselektiven 1,2-Addition von Grignard-Reagenzien an prochirale Carbonylverbindungen", Chemische Berichte, vol. 127, No. 7, Jul. 1, 1994 (Jul. 1, 1994), pp. 1323-1326.
Prisca K. Eckert et al: "Formation of Specific Configurations at Stereogenic Nitrogen Centers upon Their Coordination to Zinc and Mercury", Inorganic Chemistry, vol. 51, No. 15, Aug. 6, 2012 (Aug. 6, 2012), pp. 8516-8523.
Viktoria H. Gessner et al: "[alpha]-Lithiated (R,R)-TMCDA as an Efficient Building Block for the Preparation of Chiral N,N,O Ligands by Asymmetric 1,2-Addition" European Journal of Inorganic Chemistry, vol. 2010, No. 36, Dec. 17, 2010 (Dec. 17, 2010), pp. 5640-5649.
Peter J. Rayner et al: "Preparation and Reactions of Enantiomerically Pure [alpha]-Functionalized Grignard Reagents", Journal of the American Chemical Society, vol. 135, No. 21, May 29, 2013 (May 29, 2013), pp. 8071-8077.
Labourdette G et al: "Unusually stable chiral ethyl zinc complexes: reactivity and polymerization of lactide" Organometallics, ACS, Washington, DC, US, vol. 28 No. 5, Mar. 9, 2009 (Mar. 9, 2009) pp. 1309-1319.

(Continued)

*Primary Examiner* — Clinton A Brooks
(74) *Attorney, Agent, or Firm* — Kenealy Vaidya LLP

(57) ABSTRACT

Processes for stereoselective preparation of a chiral alcohol or a chiral amine are described. The processes include reacting a first prochiral reactant selected from the group consisting of a ketone, an aldehyde, and an imine, with a second reactant that includes a Grignard reagent, in the presence of a chiral trans-diamine of formula (1) as defined herein:

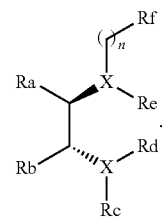

23 Claims, No Drawings

(56) References Cited

OTHER PUBLICATIONS

Kizirian J C et al: "Enantioselective addition of methyllithium to aromatic imines catalyzed by C2 symmetric tertiary diamines" Tetrahedron, Elsevier Science Publishers Amsterdam, NL, vol. 61, No. 37, Sep. 12, 2005 (Sep. 12, 2005), pp. 8939-8946.
Masui et al: "New methods and reagents in organic synthesis. 75. asymmetric synthesis of alpha-hydroxy ketones using chiral phase transfer catalysts",Tetrahedron Letters, Pergamon, GB,vol. 29 No. 23, Jan. 1, 1988 (Jan. 1, 1988) pp. 2835-2838.
Cabello, N. et al., "Simple 1,2-Diamine Ligands for Asymmetric Addition of Aryllithium Reagents to Imines", Eur. J. Org. Chem., 2005, pp. 4835-4842.
Corey, E. J. et al., A., "The Catalytic Enantioselective Construction of Molecules with Quaternary Carbon Stereocenters", Angew. Chem., Int. Ed., 1998, 37, pp. 388-401.
DiMauro, E. F. et al., "Development of Bifunctional Salen Catalysts: Rapid, Chemoselective Alkylations of a-Ketoesters", . Am. Chem. Soc. , 2002, 124, pp. 12668-12669.
Dosa, P. I. et al., "Catalytic Asymmetric Addition of ZnPh2 to Ketones: Enantioselective Formation of Quaternary Stereocenters", J. Am. Chem. Soc., 1998, 120, pp. 445-446.
Fandrick, K. R. et al., "A general copper-BINAP-catalyzed asymmetric propargylation of ketones with propargyl boronates", J. Am. Chem. Soc., 2011, 133(27), pp. 10332-10335.
Friel, D. K. et al., "Aluminum-Catalyzed Asymmetric Alkylations of Pyridyl-Substituted Alkynyl Ketones with Dialkylzinc Reagents", J. Am. Chem. Soc., 2008, 130(30), pp. 9942-9951.
Hatano, M. et al., "Recent Progress in the Catalytic Synthesis of Tertiary Alcohols from Ketones with Organometallic Reagents", Synthesis, 2008, 11, pp. 1647-1675.
Li, H. et al., "Catalytic Asymmetric Vinylation of Ketones", Am. Chem. Soc., 2004, 126, pp. 6538-6539.

Luderer, M. R. et al., "Asymmetric addition of achiral organomagnesium reagents or organolithiums to achiral aldehydes or ketones: a review", Tetrahedron: Asymmetry, 2009, 20(9), pp. 981-998.
Madduri, A. V. R. et al., "Asymmetric Copper Catalysed Addition of Grignard Reagents to Aryl Alkyl Ketones", Angewandte. Chemie Int. Ed., 2012, 51, pp. 3164-3167.
Noyori, R. et al., "Enantioselective Addition of Organometallic Reagents to Carbonyl Compounds: Chirality Transfer, Multiplication, and Amplification", Angew. Chem. Int. Ed. Engl. 1991, 30, pp. 49-69.
Noyori, R.; Suga, S.; Kawai, K.; Okada, S.; Kitamura, M., "Enantioselective alkylation of carbonyl compounds. From stoichimetric to catalytic asymmetric induction", Pure Appl. Chem. 1988, 60(11), pp. 1597-1606.
Pu, L. et al., "Catalytic asymmetric organozinc additions to carbonyl compounds", Chem. Rev. 2001, 101(3), pp. 757-824.
Ramón D. J. et al., "First enantioselective addition of dialkylzinc to ketones promoted by titanium(IV) derivatives", Tetrahedron Lett., 1998, 39, pp. 1239-1242.
Zhu, Ye et al., "Squaramide-Catalyzed Enantioselective Michael Addition of Diphenyl Phosphite to Nitroalkenes", Angew. Chem. Int. Ed., 2010, 49: pp. 153-156.
Schanz H-J et al., "Improved resolution methods for (R,R)- and (S,S)-cyclohexane-1,2-diamine and (R)- and (S)-BINOL", Tetrahedron: Asymmetry, 2003, vol. 14, No. 18, pp. 2763-2769.
Shibasaki M. et al., "Asymmetric Synthesis of Tertiary Alcohols and α-Tertiary Amines via Cu-Catalyzed C—C Bond Formation to Ketones and Ketimines", Chem. Rev., 2008, 108(8), pp. 2853-2873.
Tomita, D. et al., "Enantioselective alkenylation and phenylation catalyzed by a chiral CuF complex", J. Am. Chem. Soc., 2005, 127, pp. 4138-4139.
Weber, B. et al., "Enantiomerically Pure Tertiary Alcohols by TADDOL-Assisted Additions to Ketones—or How to Make a Grignard Reagent Enantioselective", Angew. Chem. Int. Ed. Engl. 1992, 31, pp. 84-86.
Weber, B. et al., "Highly enantioselective addition of primary alkyl Grignard reagents to carbocyclic and heterocyclic arylketones in the presence of magnesium TADDOLate preparative and mechanistic aspects", Tetrahedron, 50, 1994, pp. 6117-6128.

CHIRAL DIAMINE COMPOUNDS FOR THE PREPARATION OF CHIRAL ALCOHOLS AND CHIRAL AMINES

CROSS REFERENCE TO RELATED APPLICATION(S)

This application is a National Phase filing under 35 C.F.R. § 371 of and claims priority to PCT Patent Application No.: PCT/EP2015/061610, filed on May 26, 2015, which claims the priority benefit under 35 U.S.C. § 119 of British Application No.: 1409317.3, filed on May 26, 2014, the contents of which are hereby incorporated in their entireties by reference.

FIELD OF THE INVENTION

The present invention relates to a process for stereoselectively preparing chiral alcohols and chiral amines with a Grignard reagent.

BACKGROUND OF THE INVENTION

The Grignard reaction is one of the most commonly used methods of carbon-carbon bond formation (Grignard (1900), Richey (1999)). It is an organometallic chemical reaction in which alkyl, vinyl, or aryl magnesium halides, termed "Grignard reagents", add to an electrophilic carbon to form a carbon-carbon bond. The Grignard reagent functions as a nucleophile, attacking an electrophilic carbon atom present in a reactant molecule such a carbonyl group of a ketone or an aldehyde or a C=N group of an imine.

The addition of the Grignard reagent to an electrophilic carbon atom typically proceeds through a six-membered ring transition state, and this is shown for a ketone in the scheme below:

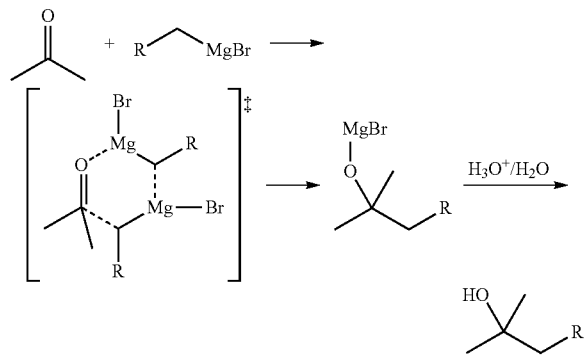

The Grignard reaction is, however, typically non-stereoselective forming racemic products such as racemic alcohols and amines.

Chiral alcohols and chiral amines are, however, essential structural motifs for a number of pharmaceutical and natural products. Thus the development of an asymmetric Grignard synthesis for these compounds is of fundamental interest.

Unfortunately, however, asymmetric C—C bond formation by the Grignard reaction is still amongst the most poorly developed fields of organic synthesis (Walsh et al. (2009); Noyori et al. (1991); Luderer et al. (2009); Corey et al. (1998)), and there are only a few examples of asymmetric 1,2-addition of a Grignard reagent to ketones (Manabu et al. (2008)).

The challenges in the development of an asymmetric Grignard reaction include:
(i) competition from background non-stereoselective reactions,
(ii) reduced enantioface discrimination when there are similar groups either side of the electrophilic carbon, and
(iii) reduced yields due to competing enolisation and reduction side reactions.

A number of strategies have been employed in the synthesis of chiral alcohols and chiral amines.

In principle, the most direct route is to resolve the racemic alcohol or amine. Resolution can be achieved using for example biological, usually enzymatic, methods. Resolution is, however, inefficient as it requires extra manufacturing steps to dispose or recycle the unwanted stereoisomer, and biological methods may also often be specific to one particular compound.

Asymmetric Grignard synthesis of alcohols and amines has previously involved transmetallation to copper, zinc, titanium or aluminium (Shibasaki et al. (2008); Fandrick et al. (2011); Tomita et al. (2005); Ashoka et al. (2012); Pu et al. (2001); DiMauro et al. (2002); Dosa et al. (1998); (Ramón (1998); Friel et al. (2008)). These methods were, however, found to have significant defects including a limited scope of reaction, an undesirable inorganic waste generation and a large excess of metal source.

Other approaches to asymmetric Grignard synthesis have used organolithium species (Noyori et al. (1988)), or organocopper species and a chiral phosphine ligand (Madduri et al. (2012)). Again, however, these approaches were found to have defects such as a limited scope of reaction and produce a low enantiomeric excess of chiral product.

Weber et al. (1992) reported a successful asymmetric 1,2-addition of Grignard reagents to ketones. However, the chiral ligand used in this process was TADDOL (α, α, α', α'-tetraaryl-1,3-dioxolan-4,5-dimethanol), which remained difficult to separate from the products and gave rise to moderate yields.

US 2004/0249184 discloses chiral phosphane ligands which are useful for the production of catalysts for asymmetric hydrosilylation, amination, alkyl substitution and Grignard coupling.

WO 99/50205 discloses a process for preparing a single enantiomer of an α,α-disubstituted-α-hydroxy acetic acid, such as cyclohexylphenylglycolic acid, using cyclic 1,2-aminoalcohols and Grignard reagents. The process involves reacting a prochiral α-ketocarboxylic acid with a single enantiomer of an N-substituted vicinal aminoalcohol of cyclopentane, cyclohexane, indane, tetralin or benzosuberane to form an ester of the α-ketocarboxylic acid, reacting this ester with an excess of a Grignard reagent to form a diastereomer of the α-hydroxycarboxylate ester, separating and optionally hydrolysing the single diastereomer to provide an α-hydroxycarboxylic acid or salt enriched in one enantiomer.

CN101844958 discloses a method for synthesising a chiral secondary alcohol using an aryl Grignard reagent, aluminium halide, a passivator, a TADDOL ligand or BINOL or BINOL derivatives thereof, and titanium tetraisopropoxide.

There therefore remains a clear need for a process which stereoselectively prepares chiral compounds using the Grignard reaction. Such a process would be particularly useful for preparing chiral alcohols and chiral amines which have important uses in developing pharmaceutical and natural products.

SUMMARY OF THE INVENTION

According to a first aspect of the present invention there is provided a process for the stereoselective preparation of a chiral alcohol or a chiral amine, the process comprising reacting a first prochiral reactant selected from the group consisting of a ketone, an aldehyde, and an imine, with a second reactant comprising a Grignard reagent, in the presence of a chiral trans-diamine of formula (1):

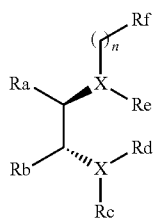

wherein X is N;

wherein Ra, Rb, Rc, Rd, and Re are each independently hydrogen, alkyl, aryl, alkenyl, cycloalkyl or cycloalkenyl; or Ra and Rb may together define a cycloalkyl or cycloalkenyl group; or Rd and Re may together with the two X atoms define a heteroaryl, heterocycloalkyl or heterocycloalkenyl group;

wherein Rf is an alkyl, alkenyl, aryl, cycloalkyl, cycloalkenyl, heteroaryl, heterocycloalkenyl or heterocycloalkyl group; and wherein n is an integer in the range of 0 to 3 (preferably n is 1);

wherein the alkyl, aryl, alkenyl, cycloalkyl, cycloalkenyl, heteroaryl, heterocycloalkenyl or heterocycloalkyl groups are optionally substituted as described herein.

The chiral trans-diamine of formula (1) is also referred to herein as a chiral additive or a chiral ligand.

In one embodiment, the prochiral ketone, aldehyde or imine may be formed in-situ.

In one embodiment, Ra and Rb together define a $C_3$-$C_7$ cycloalkyl group. Preferably the cycloalkyl group is cyclohexane or cyclopentane. In another embodiment, Ra and Rb are each independently an alkyl or an aryl group. Preferably Ra and Rb are each independently phenyl, methyl or tert-butyl.

In one embodiment Rc is a $C_{1-6}$ alkyl group and/or Rd is a $C_{1-6}$ alkyl group and/or Re is a $C_{1-6}$ alkyl group. Alternatively, Rd and Re together define an imidazolidine ring with the two N atoms and Re is a $C_{1-6}$ alkyl group.

In one embodiment, Rf is an alkyl or aryl group. Preferably Rf is a tert-butyl group.

In an alternative preferred embodiment, Rf is an aryl group which is substituted by at least one substituent selected from hydroxy, alkoxy, amino, aminoalkyl, thiol, halo, haloalkyl, haloalkoxy, alkyl, cycloalkyl, alkenyl, cycloalkenyl, alkynyl, aryl, heterocyclyl, cyano, nitro, silyl, sulfanyl, phosphanyl and $CF_3$. Particularly preferred is where Rf is phenol, aniline, N-methylaniline or dimethylaniline, each of which may be optionally substituted by one or more alkyl, alkoxy, aminoalkyl or trifluoromethyl groups.

In another preferred embodiment, Rf has the formula:

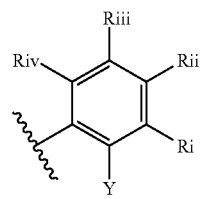

wherein

Y is a hydroxy, amino or aminoalkyl group;

Ri is selected from the group consisting of hydrogen, alkyl, alkenyl, alkynyl, aryl, cycloalkyl, silyl, halo, alkylamino, amino, alkoxy, cyano, nitro, heterocyclyl, sulfanyl, phosphanyl and trifluoromethyl; and Rii, Riii and Riv are each independently selected from the group consisting of hydrogen, alkyl, alkenyl, alkynyl, aryl, cycloalkyl, silyl, halo, aminoalkyl, amino, alkoxy, cyano, nitro, heterocyclyl, sulfanyl, phosphanyl and trifluoromethyl.

Preferably Rii and Riv are both hydrogen and/or Y is a hydroxy group. More preferably Ri and Riv are both hydrogen and Y is a hydroxy group.

Preferably, Ri is selected from the group consisting of alkyl, alkoxy, cycloalkyl, halo or trifluoromethyl, Rii and Riv are both hydrogen and Riii is selected from the group consisting of hydrogen, alkyl, alkoxy, halo, nitro or aminoalkyl.

More preferably, Ri is selected from the group consisting of methyl, tert-butyl, trifluoromethyl, adamantyl and methoxy, Rii and Riv are both hydrogen, and Riii is selected from the group consisting of hydrogen, methyl, tert-butyl, halo, N,N-dimethylamine and methoxy.

Particularly preferred is where Y is a hydroxy group, Ri is selected from the group consisting of tert-butyl, adamantyl and trifluoromethyl, Rii and Riii are both hydrogen, and Riv is selected from the group consisting of tert-butyl, bromine, hydrogen and N,N-dimethyl amine.

For example, Rf may have the formula:

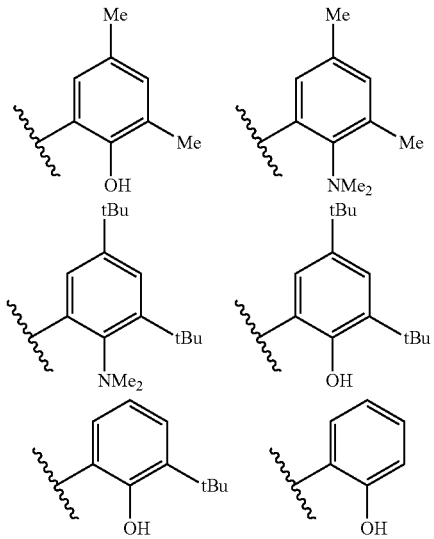

-continued
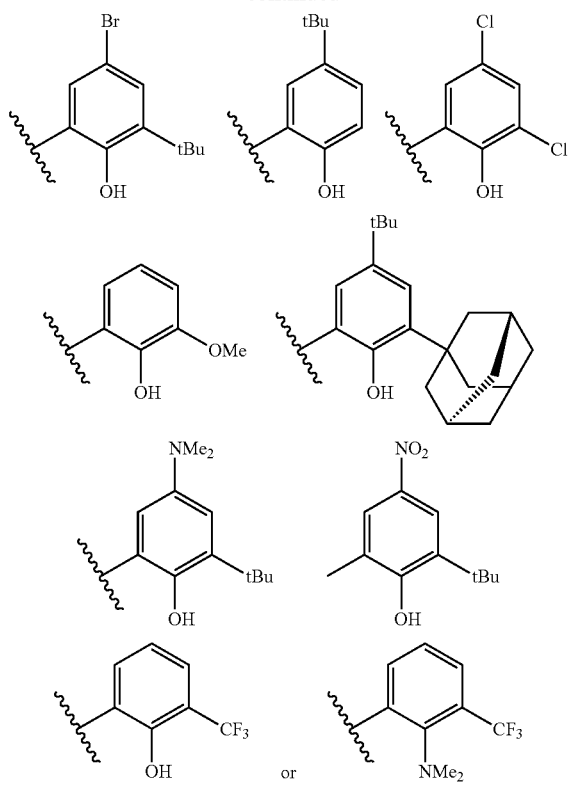
Preferably, Rf has the formula:
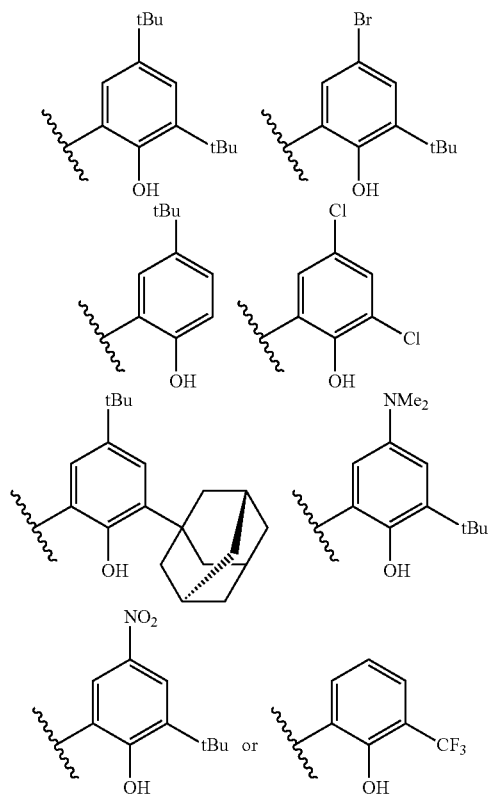
More preferably, Rf has the formula:
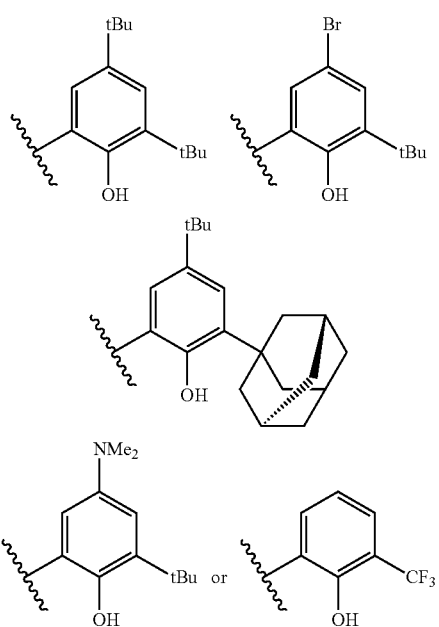
Particularly preferred is where Rf has the formula:
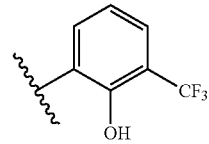 [SMILES: *c1cccc(C(F)(F)F)c1O]
In one embodiment, the chiral trans-diamine has the formula:
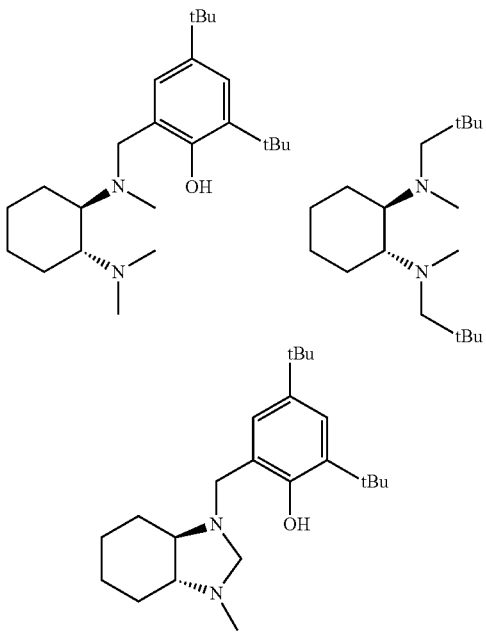

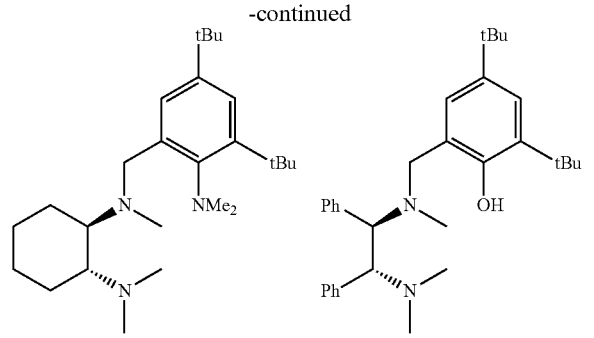
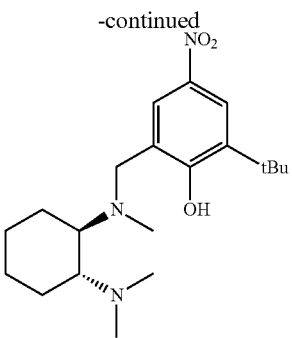
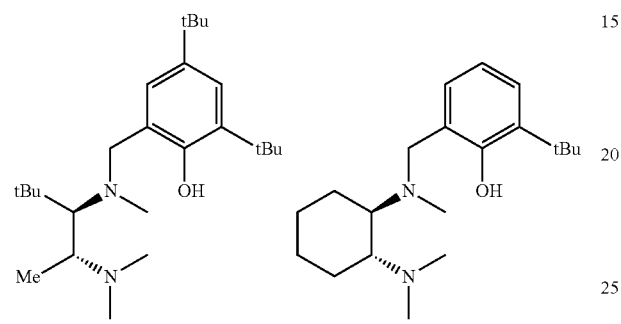
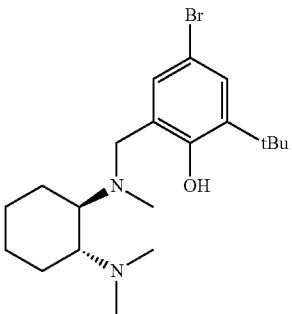
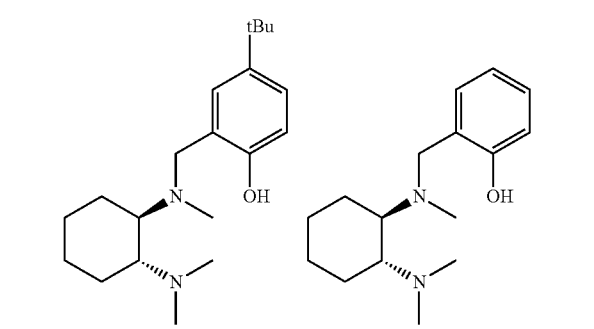
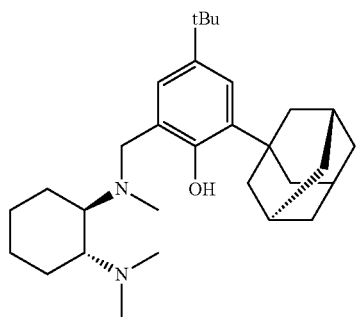
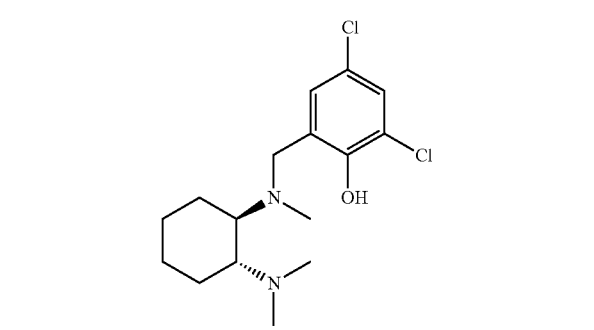
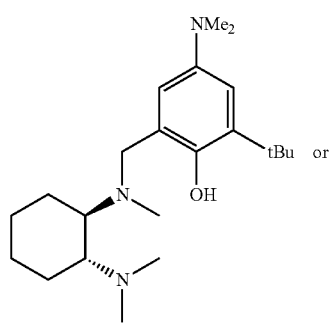
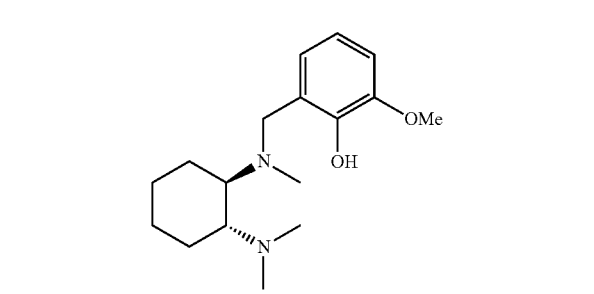
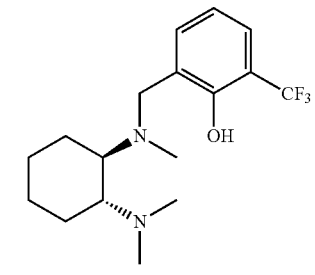 [SMILES: CN(C)[C@@H]1CCCC[C@H]1N(C)Cc1cccc(C(F)(F)F)c1O]
Preferably the chiral trans-diamine has one of the following formulae:

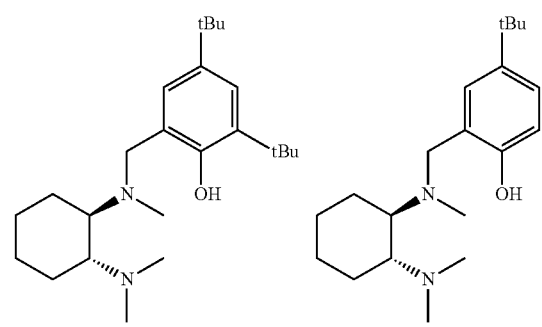
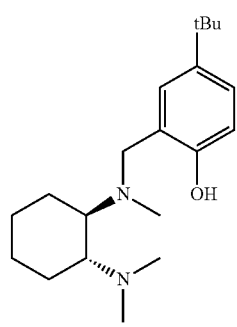
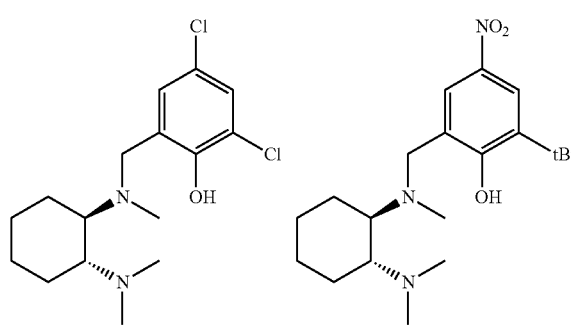
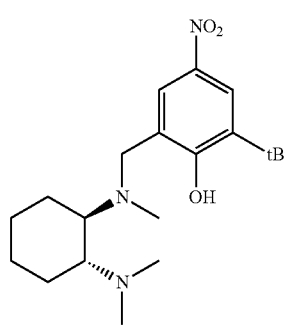
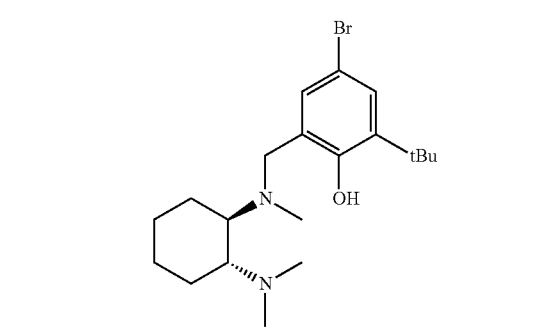
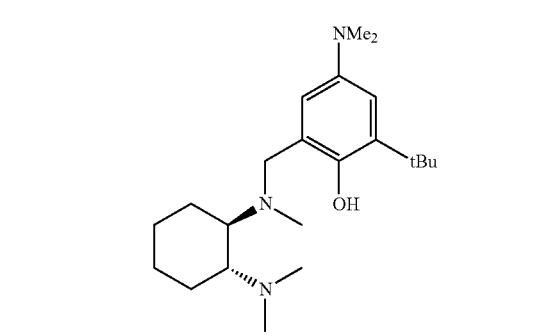
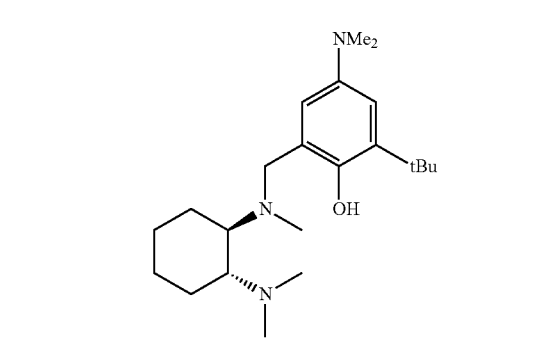
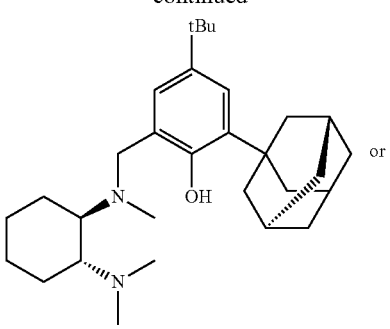
Particularly preferred is a chiral trans-diamine with a formula:
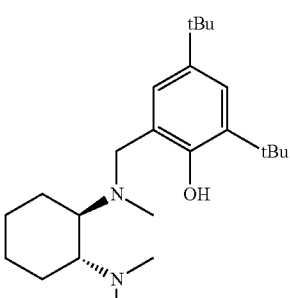
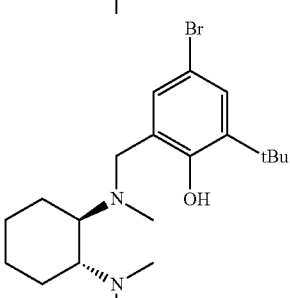
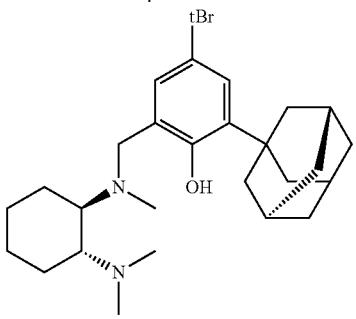

-continued

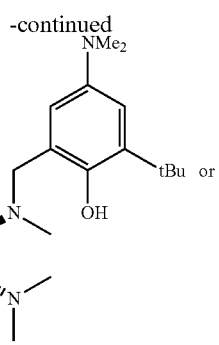
tBu or

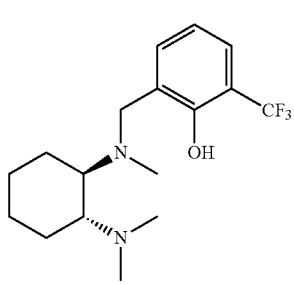

For example a chiral trans-diamine with a formula (1b):

(1b)

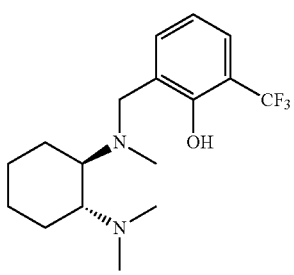 [SMILES: CN(C)[C@@H]1CCCC[C@H]1N(C)Cc1cccc(C(F)(F)F)c1O]

In one embodiment, the process of the present invention may be carried out in a solvent. Preferably the solvent includes a non-coordinating solvent and/or an ethereal solvent. Preferably a non-coordinating solvent or an ethereal solvent. Examples of such non-coordinating solvents include, but are not limited to cyclohexane, benzene, toluene, xylene, dichloromethane, pentane, cyclopentane, hexane, heptane or 1,2-difluorobenzene. Preferably the solvent is toluene. The ethereal solvent is not tetrahydrofuran or 2-methyl tetrahydrofuran.

When the first prochiral reactant of the process of the present invention comprises a ketone, the ketone may be of the formula:

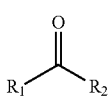

wherein $R_1$ and $R_2$ are each independently alkyl, aryl, alkenyl, cycloalkyl or cycloalkenyl; or $R_1$ and $R_2$ may together define a cycloalkyl, cycloalkenyl, heterocycloalkyl or heterocycloalkenyl group, wherein each alkyl, aryl, alk-enyl, cycloalkyl, cycloalkenyl, heterocycloalkyl or heterocycloalkenyl group may be optionally substituted as described herein. The ketone may optionally be formed in-situ in the process of the present invention.

In one embodiment, $R_1$ and $R_2$ are different.

In one embodiment $R_1$ is an alkenyl group and $R_2$ is selected from the group consisting of alkyl, aryl, alkenyl, cycloalkyl and cycloalkenyl. In one embodiment the ketone is an α, ß-unsaturated ketone.

When the first prochiral reactant of the process of the present invention comprises an aldehyde, the aldehyde may be of the formula:

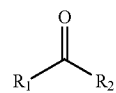

wherein $R_1$ and $R_2$ are each independently hydrogen, alkyl, aryl, alkenyl, cycloalkyl or cycloalkenyl, with the proviso that at least one of $R_1$ and $R_2$ is hydrogen; wherein each alkyl, aryl, alkenyl, cycloalkyl or cycloalkenyl group may be optionally substituted as described herein. The aldehyde may be formed in-situ in the process of the present invention.

In one embodiment, $R_1$ and $R_2$ are different and cannot both be hydrogen.

When the first prochiral reactant of the process of the present invention comprises an imine, the imine may be of the formula:

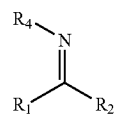

wherein $R_1$ and $R_2$ are each independently hydrogen, alkyl, aryl, alkenyl, cycloalkyl or cycloalkenyl; or $R_1$ and $R_2$ may together define a cycloalkyl, cycloalkenyl, heterocycloalkyl or heterocycloalkenyl group, wherein each alkyl, aryl, alkenyl, cycloalkyl, cycloalkenyl, heterocycloalkyl or heterocycloalkenyl group may be optionally substituted as described herein. The imine may be formed in-situ in the process of the present invention.

In one embodiment, $R_1$ and $R_2$ are different and cannot both be hydrogen.

Preferably the first prochiral reagent of the process of the invention comprises a ketone.

The Grignard reagent may be of the formula $R_3$—MgX, wherein $R_3$ is an aryl, alkyl, cycloalkyl alkenyl or alkynyl group, each of which may be optionally substituted as described herein and wherein X is halogen.

In a second aspect, the present invention provides the use of a chiral trans-diamine of formula (1) in a Grignard reaction.

In a third aspect, the present invention provides a chiral trans-diamine of formula (1) as described herein above. In one embodiment of this aspect of the invention the compound of formula (1) is not:

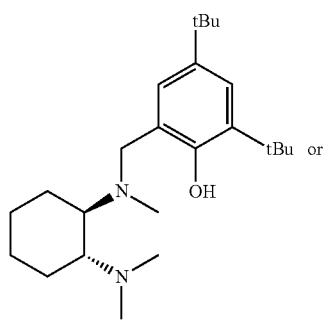
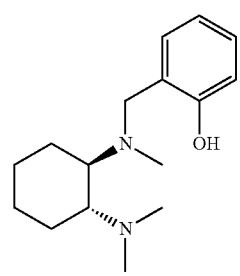
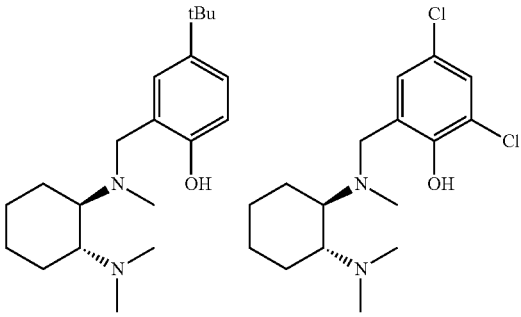
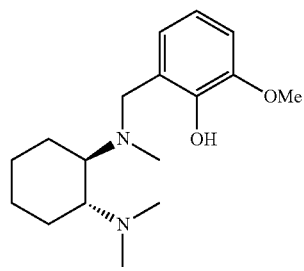
Preferably the compound of formula (1) is selected from:
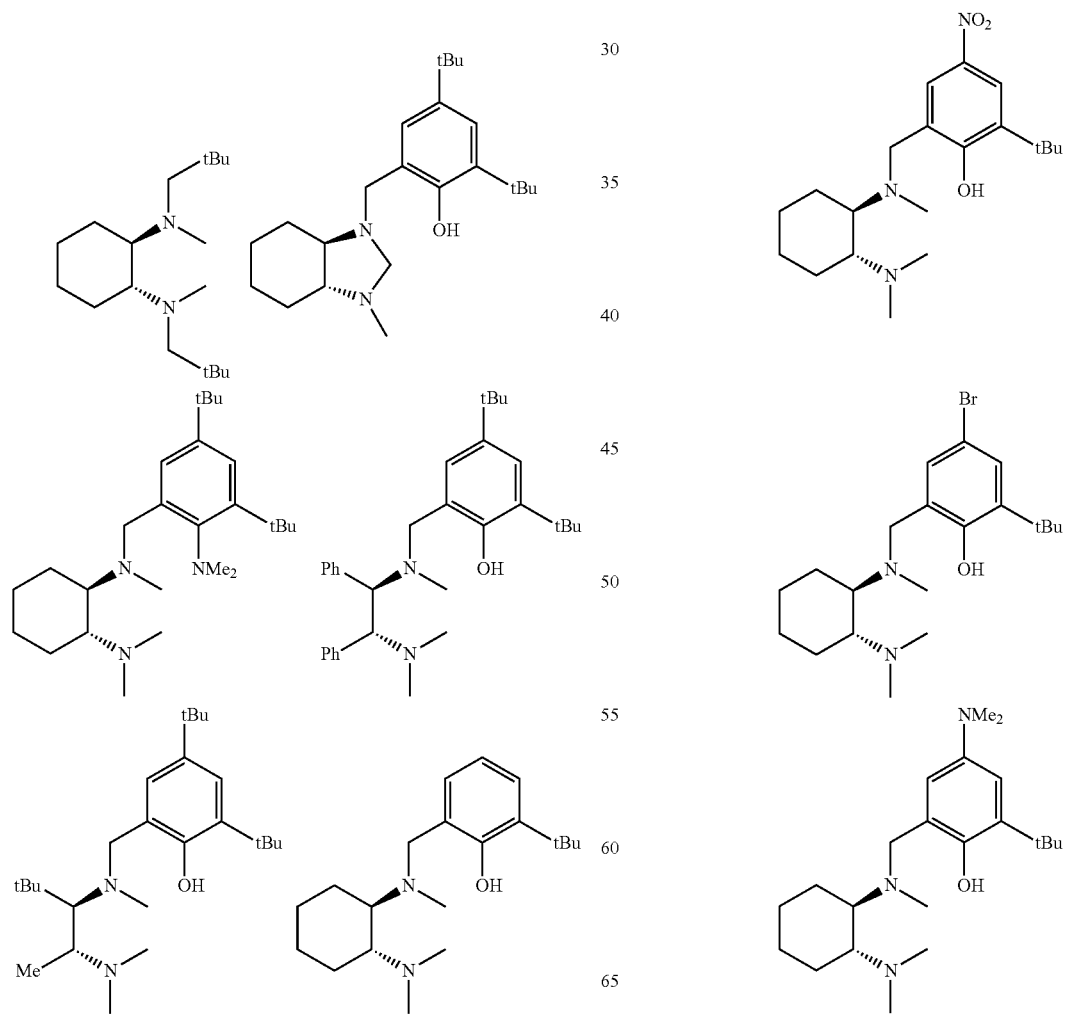

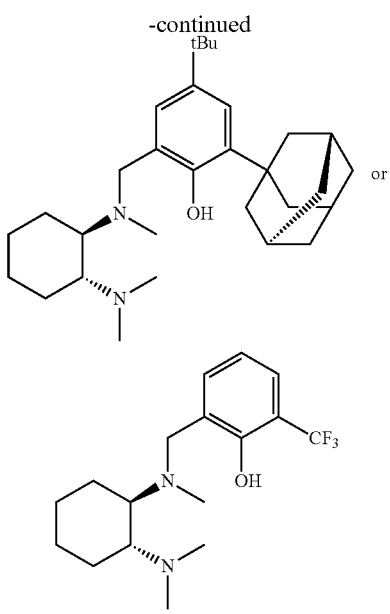

In a fourth aspect, the present invention provides a chiral trans-diamine of formula (1) as described herein above having the formula:

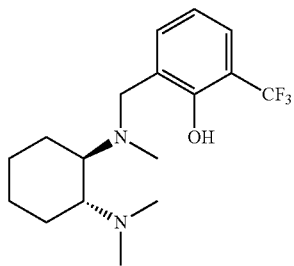

DETAILED DESCRIPTION OF THE INVENTION

Stereoselectivity

The present invention is based on the finding that chiral trans-diamines of formula (1) can be used in a Grignard reaction to stereoselectively prepare chiral alcohols or chiral amines.

The process uses the chiral trans-diamine to preferentially form one enantiomer or diastereomer of an alcohol or amine from a prochiral ketone, aldehyde or imine. Preferably from a prochiral ketone or imine. More preferably from a prochiral ketone. The provision of such a stereoselective process leads to fewer manufacturing steps, increased yields of the chiral alcohol or chiral amine, more efficient use of manufacturing capacity and less environmental impact by reducing the need to resolve these chiral compounds. The process of the present invention thus enables the stereoselective formation of carbon-carbon bonds using Grignard reagents.

The products prepared by the present invention contain at least one chiral centre. The chiral alcohol formed by the process of the present invention has a chiral centre on the carbon with the hydroxy group. The chiral alcohol may be a primary, secondary or tertiary alcohol. Preferably the chiral alcohol is a secondary or tertiary alcohol, more preferably a tertiary alcohol.

The chiral amine formed by the process of the present invention has a chiral centre on the carbon with the amino group. The chiral amine may be a primary, secondary or tertiary amine. The skilled person will appreciate that whether the alcohol or amine is primary, secondary or tertiary will depend on the nature of the first prochiral reactant.

Stereoselective reactions can be of two types: enantioselective, in which selection is between two enantiomeric products; and diastereoselective, in which selection is between diastereomeric products. The term stereoselective preparation in the present invention refers to a preparation that yields predominantly one enantiomer or one diastereomer. In one embodiment, the process of the present invention is enantioselective forming one enantiomer in preference to the other. In another embodiment, the process of the present invention is diastereoselective forming one diastereomer in preference to another.

When the process produces enantiomeric chiral products, the enantioselectivity of the process may be expressed by the enantiomeric excess (ee). A racemic mixture typically has an ee of 0%, while a completely pure enantiomer has an ee of 100%. For example, a sample with 70% of one enantiomer (e.g. R stereoisomer) and 30% of the other enantiomer (e.g. S stereoisomer) has an ee of 40%. This may also be called a scalemic mixture or a non-racemic mixture, where the ratio of enantiomers in the mixture is other than 1:1.

In one embodiment the process is enantioselective, and the chiral alcohol or chiral imine may be prepared with an enantiomeric excess (ee) of greater than about 40%. In another embodiment the enantiomeric excess is greater than about 50%. In another embodiment the enantiomeric excess is greater than about 60%. In another embodiment the enantiomeric excess is greater than about 70%. In another embodiment the enantiomeric excess is greater than about 80% or greater than about 90%.

In one embodiment said chiral alcohol or chiral amine is substantially homochiral, preferably having greater than 95% ee, more preferably having greater than 99% ee.

When the process produces diastereomeric chiral products, the diastereoselectivity of the process may be expressed by the diastereomeric excess (de).

In one embodiment the process is diastereoselective, and the chiral amine or chiral imine may be produced with a diastereomeric excess (de) of greater than about 40%. In another embodiment the de is greater than about 50%, greater than about 60% or greater than about 70%. In another embodiment the de is greater than about 80% or greater than about 90%. In another embodiment the de is greater than about 95%. In another embodiment the de is greater than about 99%.

Grignard Reagent

The process of the present invention uses a Grignard reagent. The nature of the Grignard reagent is not particularly limited, and may be produced in-situ according to methods known in the art.

For example, the Grignard reagent may be made by adding an organic halide to a suspension of magnesium in an ethereal solvent. The reaction should be dry (i.e. water and air should be substantially excluded). Alternatively the Grignard reagent may be a commercially available material.

In one embodiment, the Grignard reagent is of the formula $R_3$—MgX, wherein $R_3$ is an aryl, cycloalkyl, alkyl, alkenyl or alkynyl group, each of which may be optionally substituted as described herein and wherein X is a halogen. Preferably X is iodine, bromine or chlorine, more preferably X is bromine or iodine, e.g. bromine.

In one embodiment $R_3$ is alkyl. For example, $R_3$ may be an alkyl group and X may be bromine, chlorine or iodine. Particularly preferred alkyl Grignard reagents include methylmagnesium bromide, methylmagnesium chloride, methylmagnesium iodide, iso-butylmagnesiumbromide, iso-propylmagnesium bromide, propylmagnesium bromide, butyl magnesium bromide, ethylmagnesium bromide and ethylmagnesium iodide.

In another embodiment, $R_3$ is aryl. For example $R_3$ may be an aryl group and X may be bromine or iodine. Particularly preferred Grignard reagents include phenylmagnesium bromide, phenylmagnesium iodide, methylphenylmagnesium iodide, 1-naphthylmagnesium bromide and 2-naphthylmagnesium bromide.

In a further embodiment, $R_3$ is a cycloalkyl group where the cycloalkyl is preferably cyclopentane or cyclohexane. For example, the Grignard reagent may be cyclopentanemagnesium bromide or cyclohexanemagnesium bromide.

In a further embodiment, $R_3$ is an alkenyl group. For example the Grignard reagent may be allylmagnesium bromide or vinylmagnesium bromide.

In a further embodiment, $R_3$ is an alkynyl group. For example the Grignard reagent may be ethynylmagnesium bromide or phenylethynylmagnesium bromide.

The alkyl, aryl, cycloalkyl, alkenyl and alkynyl groups may be substituted as described herein.

The Grignard reaction is based on a reaction system comprising a Grignard reagent and a reactant including an electrophilic carbon. In the process of the present invention, the reagent including an electrophilic carbon—otherwise termed the first reactant—is prochiral and the electrophilic carbon may be present in a ketone, an aldehyde or an imine moiety. The ketone, aldehyde or imine may optionally be formed in-situ.

When the first prochiral reactant comprises a ketone, the process of the present invention may be generally represented by Scheme 1:

Scheme 1

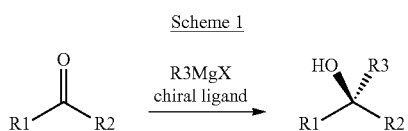

wherein $R_3$ and X are as defined above and $R_1$ and $R_2$ are each independently alkyl, alkenyl, aryl, cycloalkyl or cycloalkenyl. $R_1$ and $R_2$ may also together define a cycloalkyl, cycloalkenyl, heterocycloalkyl or heterocycloalkenyl group. The alkyl, alkenyl, aryl, cycloalkyl, cycloalkenyl, heterocycloalkyl or heterocycloalkenyl group may be optionally substituted as described herein. Preferably $R_1$ and $R_2$ are different.

When the first prochiral reactant comprises an aldehyde, the process of the present invention may be generally represented by Scheme 1 above, wherein $R_3$ and X are as defined above and $R_1$ and $R_2$ are each independently hydrogen, alkyl, alkenyl, aryl, cycloalkyl or cycloalkenyl, provided that at least one of $R_1$ and $R_2$ is hydrogen. The alkyl, alkenyl, aryl, cycloalkyl or cycloalkenyl group may be optionally substituted as described herein. Preferably $R_1$ and $R_2$ are different and cannot both be hydrogen.

When the first prochiral reactant comprises an imine, the process of the present invention may be generally represented by Scheme 2:

Scheme 2

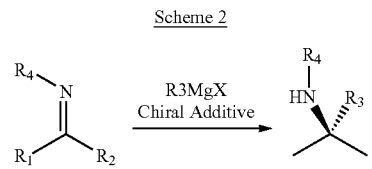

wherein $R_3$ and X are as defined above, wherein $R_1$ and $R_2$ are each independently hydrogen, alkyl, alkenyl, aryl, cycloalkyl or cycloalkenyl. $R_1$ and $R_2$ may also together define a cycloalkyl, cycloalkenyl, heterocycloalkyl or heterocycloalkenyl group. $R_4$ may be hydrogen, alkyl, alkenyl, aryl, cycloalkyl, cycloalkenyl, heterocycloalkyl or heterocycloalkenyl group. The alkyl, alkenyl, aryl, cycloalkyl, cycloalkenyl, heterocycloalkyl or heterocycloalkenyl groups may be optionally substituted as described herein. Preferably $R_1$ and $R_2$ are different and cannot both be hydrogen.

By the ketone, aldehyde or imine being formed in-situ is meant that the ketone, aldehyde or imine is formed during the reaction to form a chiral alcohol or a chiral amine. For instance, the ketone, aldehyde or imine may be formed from a starting material prior to the reaction of the first reactant with the Grignard reagent in the presence of the chiral trans-diamine of formula (1). In-situ methods of forming a ketone, aldehyde or imine are known in the art.

In one embodiment, the ketone may be formed in-situ from the addition of excess Grignard reagent to a starting material selected from the group consisting of an ester, an acid halide, an acid anhydride, a thioester, an amide, a N-methoxyamide, a carboxylic acid, an epoxide and a cyanide. For example, "excess" may refer to the use of two equivalents of the Grignard reagent with one equivalent of the starting material.

The chiral trans-diamine may be added with the excess Grignard reagent or after the ketone, aldehyde or imine has been formed in-situ.

The reaction conditions for the above-mentioned Grignard reactions may be as known in the art (see e.g. Smith, M. B. and J. March, Advanced Organic Chemistry: Reactions, Mechanisms, and Structure, 6th edition (Wiley, 2007); and Silverman, G, S. and Rakita, P. E., Handbook of Grignard Reagents (CRC Press, 25 Apr. 1996).

The reaction conditions may also include those taught herein.

In one embodiment the Grignard reaction is carried out at a low temperature, for example at 0° C. or below. Preferably at between 0° C. and −80° C., −10° C. and −50° C., −20° C. and −80° C. e.g. at −20° C.

In one embodiment the solvent used for the Grignard reaction comprises an ethereal solvent, i.e. the solvent contains at least one C—O—C bond. Typical ethereal solvents include diethyl ether, methyl tert-butyl ether, o-anisole, 2,5-dimethyl tetrahydrofuran, dioxane, and glyme (dimethoxyethane).

In a preferred embodiment, the solvent comprises a non-coordinating solvent. Preferably the solvent includes a non-coordinating solvent selected from cyclohexane, toluene, benzene, xylene, hexane, 1,2-difluorobenzene, dichloromethane, pentane, cyclopentane and heptanes. A particularly preferred non-coordinating solvent is toluene.

In a particularly preferred embodiment the non-coordinating solvent (e.g. toluene) may be used in the presence of another solvent. In one embodiment, the non-coordinating solvent is used with an ethereal solvent, such as diethyl ether, dibutyl ether, tert-butyl methyl ether, o-anisole, 2,5- dimethyl tetrahydrofuran or glyme (dimethoxyethane). In one embodiment, the non-coordinating solvent is the main solvent in the solvent mixture and the ethereal solvent is present in a minor amount, e.g. as an additive.

In an especially preferred embodiment, the ethereal solvent is not tetrahydrofuran or 2-methyl tetrahydrofuran.

In another embodiment, the solvent used for the Grignard reaction is an ethereal solvent or a non-coordinating solvent, with the proviso that the ethereal solvent is not tetrahydrofuran or 2-methyl tetrahydrofuran. The solvent is preferably selected from the group consisting of toluene, diethyl ether, methyl tert-butyl ether, and 2,5-dimethyl tetrahydrofuran.

In one embodiment, the Grignard reaction may be carried out in the presence of a stable radical species. Suitable stable radical species are known in the art.

Preferably the stable radical species is (2,2,6,6-tetramethylpiperidin-1-yl)oxyl also known as TEMPO, having the following structure:

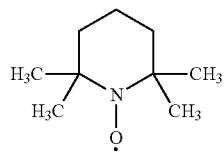

Chiral Ligand

The process of the present invention is carried out in the presence of a chiral ligand. Without wishing to be bound by theory, the present inventors believe that the chiral ligand described herein coordinates to the magnesium of the Grignard reagent, and the coordinated ligand-Grignard product then approaches the electrophilic carbon of the first reactant (e.g. in the carbonyl group of a ketone) preferentially from one face resulting in stereoselective 1,2-addition to yield a chiral product (e.g. a chiral alcohol) in high enantiomeric or diastereomeric excess.

The chiral ligand used in the present invention is a chiral trans-diamine of structural formula (1):

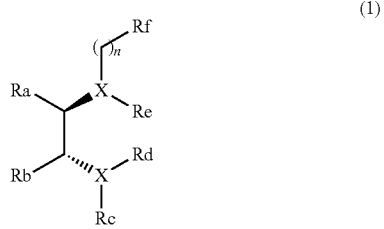

wherein X is N;

wherein Ra, Rb, Rc, Rd, and Re are each independently hydrogen, alkyl, aryl, alkenyl, cycloalkyl or cycloalkenyl; or Ra and Rb may together define a cycloalkyl or cycloalkenyl group; or Rd and Re may together with the two X atoms define a heterocycloalkyl or heterocycloalkenyl group;

wherein Rf is an alkyl, alkenyl, aryl, cycloalkyl, cycloalkenyl, heteroaryl, heterocycloalkenyl or heterocycloalkyl group; and n is an integer in the range of 0 to 3, preferably n is 1 or 2, more preferably n is 1;

wherein the alkyl, aryl, alkenyl, cycloalkyl, cycloalkenyl, heteroaryl, heterocycloalkenyl or heterocycloalkyl groups are optionally substituted as described herein.

The chiral trans-diamine may be an enantiomerically enriched or an enantiomerically pure trans compound.

In one embodiment, Ra and Rb together define a $C_3$-$C_7$ cycloalkyl group. Preferably Ra and Rb together define a $C_4$-$C_6$ cycloalkyl group, more preferably the cycloalkyl group is cyclohexane or cyclopentane. Particularly preferred are compounds where Ra and Rb together define a cyclohexane group.

Alternatively, Ra and Rb are each independently an alkyl or an aryl group. In one embodiment, both Ra and Rb are alkyl groups. In another embodiment, both Ra and Rb are aryl groups. In one embodiment, Ra and Rb are each independently a phenyl or a $C_{1-6}$ alkyl group. Preferably Ra and Rb are each independently phenyl, methyl, ethyl, n-propyl, iso-propyl, n-butyl, iso-butyl, sec-butyl, or tert-butyl. Preferably Ra and Rb are each independently phenyl, methyl, or tert-butyl.

In one embodiment, Rc, Rd and Re are each independently an alkyl group. In one embodiment, Rc, Rd and Re are each independently a $C_{1-6}$ alkyl group. Preferably an alkyl group selected from methyl, ethyl, n-propyl, iso-propyl, n-butyl, iso-butyl, sec-butyl, or tert-butyl. More preferably an alkyl group selected from methyl, ethyl, n-propyl and n-butyl. Particularly preferred is a methyl group.

In another embodiment, Rd and Re together define a heterocyclyl ring with the two X atoms. The heterocyclyl ring may be a heterocycloalkyl, heterocycloalkenyl or heteroaryl ring. In one embodiment, Rd and Re together define a heterocycloalkyl ring with the two X atoms. Preferably Rd and Re together define a five to seven membered ring containing the two X atoms. Preferred heterocycloalkyl groups include imidazolidine and piperazine. Particularly preferred is the imidazolidine ring.

In another embodiment, Rd and Re taken together define a heteroaryl ring with the two X atoms. In one embodiment Rd and Re together define a five or six membered aromatic ring. Preferred heteroaryl groups include pyrazines and imidazole.

In one embodiment, Ra and Rb together define a $C_3$-$C_7$ cycloalkyl group and Rc, Rd and Re are $C_{1-6}$ alkyl groups or Rc is a $C_{1-6}$ alkyl group and Rd and Re taken together form a heterocycloalkyl group with the two X atoms, e.g. imidazolidine.

In another embodiment, Ra and Rb together define a cyclohexane group and Rc, Rd and Re are each methyl groups. In a further embodiment, Ra and Rb together define a cyclohexane group, Rc is a methyl group and Rd and Re taken together form an imidazolidine ring with the two X atoms. In another embodiment, Ra and Rb together define a cyclohexane group, Rc is a methyl group substituted by tert-butyl and Rd and Re are both methyl groups.

In another embodiment, Ra and Rb are both phenyl groups and Rc, Rd and Re are each methyl groups.

In another embodiment, Ra is a tert-butyl group, and Rb, Rc, Rd and Re are each methyl groups.

In one embodiment, Rf is an alkyl, or an aryl group. In another embodiment Rf is an alkyl group, preferably a $C_{1-6}$ alkyl group, e.g. a methyl, ethyl, propyl or butyl group. More preferably, Rf is a propyl or butyl group, e.g. a tert-butyl group.

In another embodiment, Rf is an aryl group. Preferably the aryl group is a phenyl. In one embodiment, Rf is an aryl group which is substituted by at least one substituent. Preferably Rf is an aryl group which is substituted by at least two substituents, more preferably at least three substituents.

In one embodiment, Rf is a phenyl group which is substituted by at least one substituent at the 2-position. Preferably the substituent includes a heteroatom such as oxygen, nitrogen, phosphorus or sulphur. Particularly preferred substituents include hydroxy, alkoxy, amino, aminoalkyl, thiol, acyl, halo, haloalkyl, haloalkoxy, nitro, cyano, phosphine and sulfhydryl. For example, a hydroxy, amino or aminoalkyl group. Most preferred is a hydroxy group.

In one embodiment, Rf is a phenyl group which is substituted by at least one substituent in the 2-position. The substituents in the 2-position are as defined above, preferably the substituent is a hydroxy, amino or aminoalkyl group such that Rf is a phenol, aniline, N-methylaniline or dimethylaniline group, each of which may be optionally substituted.

In another embodiment, Rf is a phenyl group which is substituted by at least two substituents. One of the substituents is in the 2-position and the at least one other substituent is in the 3-, 4-, 5- or 6-position on the benzene ring. This substitution pattern may also be described as the at least one other substituent being ortho-, meta- or para- to the substituent at the 2-position.

Preferably Rf is a phenyl group with at least two substituents in the 2- and 3-, 2- and 4-, 2- and 5-, or 2- and 6-positions. In one embodiment, Rf is a phenyl group which is substituted by at least two substituents, preferably one substituent in the 2-position and at least one substituent in the 3- or 5-positions. For example, Rf may be a phenyl group with at least two substituents in the 2- and 3-positions, or in the 2- and 5-positions. Rf may also be a phenyl group with three substituents in the 2-, 3- and 5-, 2-, 3- and 4-, or 2-, 3- and 6-, positions on the benzene ring. Particularly preferred is Rf being a phenyl group with substituents in the 2-, 3- and 5- or 2- and 3-positions.

The substituents on the Rf group may be selected from the group consisting of hydroxy, alkoxy, amino, aminoalkyl, thiol, acyl, halo, haloalkyl, haloalkoxy, alkyl, cycloalkyl, alkenyl, cycloalkenyl, alkynyl, aryl, heterocyclyl, cyano, nitro, silyl, sulfanyl, phosphanyl and $CF_3$.

Preferably the substituents are selected from hydroxy, alkoxy, amino, aminoalkyl, alkyl, alkenyl, alkynyl, cycloalkyl, silyl, halo, nitro, cyano, heterocyclyl, sulfanyl, phosphanyl, trifluoromethyl and aryl.

More preferably the substituents are selected from hydroxy, amino, aminoalkyl, $C_{1-6}$-alkyl, $C_{1-6}$-alkenyl, $C_{1-6}$-alkynyl, phenyl, mesityl, benzyl, adamantyl, trimethylsilyl, triphenylsilyl, iodine, bromine, chlorine, fluorine, cyano, pyridyl, sulfanyl, phosphanyl, nitro and trifluoromethyl. Most preferably the substituents are selected from hydro, amino, aminoalkyl, tert-butyl, adamantyl, bromine, chlorine, nitro and trifluoromethyl.

Particularly preferred is where a hydroxy, amino or aminoalkyl substituent is the at least one substituent in the 2-position of Rf when Rf is a phenyl ring. The other substituents on the phenyl ring may then be selected from the group consisting of amino, aminoalkyl, $C_{1-6}$-alkyl, $C_{1-6}$-alkenyl, $C_{1-6}$-alkynyl, phenyl, mesityl, benzyl, adamantyl, trimethylsilyl, triphenylsilyl, iodine, bromine, chlorine, fluorine, cyano, pyridyl, sulfanyl, phosphanyl, nitro and trifluoromethyl.

Preferably methyl, ethyl, n-propyl, isopropyl, n-butyl, sec-butyl, tert-butyl, n-pentyl, tert-pentyl, neo-pentyl, isopentyl, sec-pentyl, 4-pentyl, phenyl, mesityl, benzyl, adamantyl, trimethylsilyl, triphenylsilyl, iodine, bromine, chlorine, fluorine, cyano, pyridyl, sulfanyl, phosphanyl, nitro and trifluoromethyl.

In one embodiment, Rf is phenol, aniline, N-methylaniline or dimethylaniline, each of which may be optionally substituted by one or more substituents selected from the group consisting of hydroxy, alkoxy, amino, aminoalkyl, thiol, halo, haloalkyl, haloalkoxy, alkyl, cycloalkyl, alkenyl, cycloalkenyl, aryl, cyano, nitro and $CF_3$. Preferably Rf is phenol, aniline, N-methylaniline or dimethylaniline, each optionally substituted by one or more alkyl, cycloalkyl, alkoxy, aminoalkyl, halo, nitro or trifluoromethyl ($CF_3$) groups.

In one embodiment, Rf has the formula:

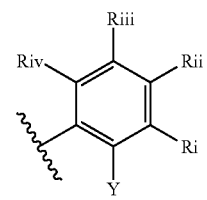

wherein
Y is a hydroxy, amino or aminoalkyl group;
Ri is selected from the group consisting of hydrogen, alkyl, alkenyl, alkynyl, aryl, cycloalkyl, silyl, halo, alkylamino, amino, alkoxy, cyano, nitro, heterocyclyl, sulfanyl, phosphanyl and trifluoromethyl; and
Rii, Riii and Riv are each independently selected from the group consisting of hydrogen, alkyl, alkenyl, alkynyl, aryl, cycloalkyl, silyl, halo, aminoalkyl, amino, alkoxy, cyano, nitro, heterocyclyl, sulfanyl, phosphanyl and trifluoromethyl.

Preferably, Y is a hydroxy, amino, NH($C_{1-6}$-alkyl) or N($C_{1-6}$-alkyl)$_2$ group. More preferably, Y is a hydroxy, amino, NH(methyl) or N(methyl)$_2$ group. Most preferably Y is a hydroxy group.

Preferably Ri is selected from the group consisting of hydrogen, $C_{1-6}$-alkyl, $C_{1-6}$-alkenyl, $C_{1-6}$-alkynyl, phenyl, mesityl, benzyl, adamantyl, Si($C_{1-6}$-alkyl)$_3$, triphenylsilyl, iodine, bromine, chlorine, fluorine, aminoalkyl, cyano, pyridyl, pyrimidyl, pyrrolyl, furanyl, thiophenyl, sulfanyl, phosphanyl, and trifluoromethyl. More preferably, Ri is selected from the group consisting of methyl, ethyl, n-propyl, isopropyl, n-butyl, sec-butyl, tert-butyl, n-pentyl, tert-pentyl, neo-pentyl, isopentyl, sec-pentyl, 4-pentyl, phenyl, mesityl, benzyl, adamantyl, trimethylsilyl, triphenylsilyl, iodine, bromine, chlorine, fluorine, N,N-dimethylamine, cyano, pyridyl, pyrimidyl, pyrrolyl, furanyl, thiophenyl, sulfanyl, phosphanyl, and trifluoromethyl. Particularly preferred is where Ri is tert-butyl, adamantyl, bromine, chlorine, trifluoromethyl or methoxy. For example, Ri may be tert-butyl, adamantyl, bromine, or trifluoromethyl.

Preferably Rii and Riv are each independently selected from the group consisting of hydrogen, $C_{1-6}$-alkyl, $C_{1-6}$-alkenyl, $C_{1-6}$-alkynyl, phenyl, mesityl, benzyl, adamantyl, Si($C_{1-6}$-alkyl)$_3$, triphenylsilyl, iodine, bromine, chlorine, fluorine, aminoalkyl, cyano, pyridyl, pyrimidyl, pyrrolyl, furanyl, thiophenyl, sulfanyl, phosphanyl, and trifluoromethyl. More preferably, Rii and Riv are each independently is selected from the group consisting of hydrogen, methyl, ethyl, n-propyl, isopropyl, n-butyl, sec-butyl, tert-butyl, n-pentyl, tert-pentyl, neo-pentyl, isopentyl, sec-pentyl, 4-pentyl, phenyl, mesityl, benzyl, adamantyl, trimethylsilyl, triphenylsilyl, iodine, bromine, chlorine, fluorine, N,N-dimethylamine, cyano, pyridyl, pyrimidyl, pyrrolyl, furanyl, thiophenyl, sulfanyl, phosphanyl, and trifluoromethyl. Particularly preferred is where Rii and Riv are both hydrogen.

Preferably Riii is selected from the group consisting of hydrogen, $C_{1-6}$-alkyl, $C_{1-6}$-alkenyl, $C_{1-6}$-alkynyl, phenyl, mesityl, benzyl, adamantyl, $Si(C_{1-6}$-alkyl$)_3$, triphenylsilyl, iodine, bromine, chlorine, fluorine, aminoalkyl, nitro, cyano, pyridyl, pyrimidyl, pyrrolyl, furanyl, thiophenyl, sulfanyl, phosphanyl, and trifluoromethyl. More preferably, Riii is selected from the group consisting of hydrogen, methyl, ethyl, n-propyl, isopropyl, n-butyl, sec-butyl, tert-butyl, n-pentyl, tert-pentyl, neo-pentyl, isopentyl, sec-pentyl, 4-pentyl, phenyl, mesityl, benzyl, adamantyl, trimethylsilyl, triphenylsilyl, iodine, bromine, chlorine, fluorine, N,N-dimethylamine, nitro, cyano, pyridyl, pyrimidyl, pyrrolyl, furanyl, thiophenyl, sulfanyl, phosphanyl, and trifluoromethyl. Particularly preferred is where Riii is selected from the group consisting of hydrogen, tert-butyl, bromine, chlorine, nitro, N,N-dimethylamine and methoxy. For example, Riii may be selected from hydrogen, tert-butyl, bromine, and N,N-dimethylamine.

In one embodiment, Ri is selected from the group consisting of alkyl, alkoxy, cycloalkyl, halo, and trifluoromethyl, Rii and Riv are both hydrogen and Riii is selected from the group consisting of hydrogen, alkyl, alkoxy, halo (e.g. bromine or chlorine), nitro and aminoalkyl.

Preferably Ri is selected from the group consisting of methyl, tert-butyl, trifluoromethyl, adamantyl and methoxy, Rii and Riv are both hydrogen and Riii is selected from the group consisting of hydrogen, methyl, tert-butyl, halo (e.g. bromine or chlorine), N,N-dimethylamine and methoxy.

More preferably Ri is selected from the group consisting of tert-butyl, trifluoromethyl, and adamantyl, Rii and Riv are both hydrogen and Riii is selected from the group consisting of hydrogen, tert-butyl, bromine, and N,N-dimethylamine.

In one embodiment, Rf has the formula:

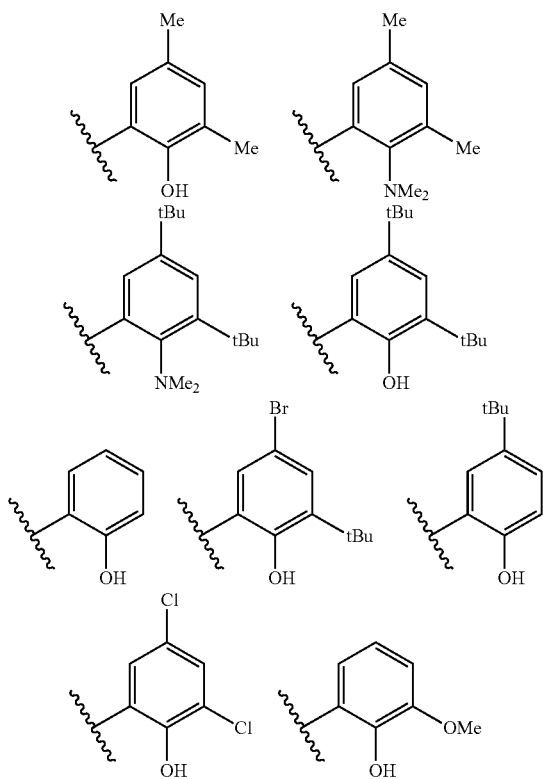

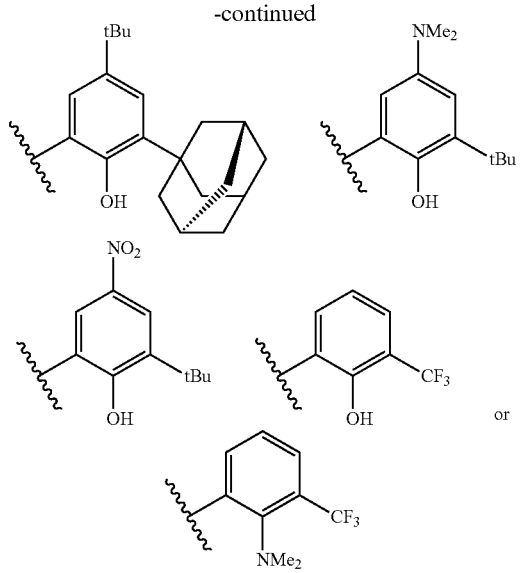

The chiral trans-diamine of formula (1) can easily be removed from the reaction mixture. In one embodiment, the process of the present invention further includes separating the chiral ligand from said reaction mixture. For example by acid-base extraction or recrystallisation. Preferably acetic acid is used in an acid-base extraction.

By way of example, a crude reaction mixture from an enantioselective addition of Grignard reagent to a ketone may be washed with acetic acid (e.g. at 10%, for 3-5 times using 50 vol.). Aqueous layers may then be combined and basified with a base such as 5M NaOH, leading to a formation of white precipitation. Solids may then be extracted into diethyl ether (e.g. 2×50 vol.), washed with water (e.g. 50 vol.) and dried over $MgSO_4$. Solvent may then be removed in vacuo to yield crude recovered ligand, which can be further purified by recrystallization from e.g. hot isopropyl alcohol (IPA)/water (2:1).

General Definitions

As used herein, the term "alkyl" includes both saturated straight chain and branched alkyl groups which may be substituted (mono- or poly-) or unsubstituted. Preferably, the alkyl group is a $C_{1-15}$ alkyl group, more preferably a $C_{1-10}$ alkyl group, more preferably still a $C_{1-8}$ alkyl group, more preferably still a $C_{1-6}$ alkyl group. Particularly preferred alkyl groups include, for example, methyl, ethyl, n-propyl, iso-propyl, n-butyl, sec-butyl, tert-butyl, n-pentyl, tert-pentyl, neo-pentyl, iso-pentyl, sec-pentyl and 4-pentyl.

As used herein, the term "aryl" refers to a $C_{6-18}$ aromatic group which may be substituted (mono- or poly-) or unsubstituted. Preferably the aryl group is a $C_{6-14}$ aryl group, more preferably a $C_{6-10}$ aryl group. Typical examples include phenyl, naphthyl, mesityl, benzyl, and anthracenyl, and a particularly preferred aryl group is phenyl, napthyl, mesityl or benzyl, e.g. phenyl or napthyl, particularly phenyl.

As used herein, the term "alkenyl" refers to a carbon chain containing one or more carbon-carbon double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably still a $C_{2-10}$ alkenyl group, more preferably still a $C_{2-8}$ alkenyl group, or more preferably still a $C_{2-6}$ alkenyl group.

As used herein, the term "alkynyl" refers to a carbon chain containing one or more carbon-carbon triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, more preferably still a $C_{2-8}$ alkynyl group, or more preferably still a $C_{2-6}$ alkynyl group.

As used herein, the term "cycloalkyl" refers to a mono- or multi-ringed cyclic alkyl group which may be substituted (mono- or poly-) or unsubstituted. Preferably the cycloalkyl is a mono-ringed group. Preferably a $C_3$-$C_7$ cycloalkyl group, particularly preferred are cyclopentane, cyclohexane and cycloheptane groups, e.g. cyclopentane or cyclohexane. In another embodiment, the cycloalkyl is a multi-ringed group, e.g. adamantyl.

As used herein, the term "cycloalkenyl" refers to a cyclic alkenyl group which may be substituted (mono- or poly-) or unsubstituted. Preferably the cycloalkenyl is a monocyclic group. Preferably a $C_3$-$C_7$ cycloalkenyl group, particularly preferred are cyclopentene, cyclohexene and cycloheptene groups, e.g. cyclopentene or cyclohexene.

As used herein, the term "heterocyclyl" refers to heteroaryl, heterocycloalkyl and heterocycloalkenyl groups.

The term "heteroaryl" refers to an aryl group as defined above wherein at least one ring atom is a heteroatom. Suitable heteroatoms will be apparent to those skilled in the art and include, for example, sulphur, nitrogen, oxygen, phosphorus and silicon. Particularly preferred is when the heteroatom is sulphur, nitrogen or oxygen.

Monocyclic heteroaryl groups include for example, furan, pyrrole, thiophene, imidazole, oxazole, thiazole, 1,3,4-thiadiazole, isothiazole, isoxazole, oxadiazole, oxazole, 1,2,3-oxadiazole, pyrazole, triazole, tetrazole, pyridine, pyrazine, pyrimidine, pyridazines, triazine and tetrazine. Bicyclic or polycyclic heteroaryl groups may include a monocyclic heteroaryl group as defined herein, fused to one or more groups independently selected from an aryl group, a cycloalkyl group, a cycloalkenyl group and another monocyclic heteroaryl group. For example, the heteroaryl group may be indole, benzimidazole, benzothiazole, benzofuran, indoline, quinolone, isoquinoline, isoindole, indazole, phenylpiperidine or benzothiene.

The terms "heterocycloalkyl" and "heterocycloalkenyl" respectively refer to a cycloalkyl group or a cycloalkenyl group as defined above, wherein at least one ring atom in the cycloalkyl or cycloalkenyl group is a heteroatom. Again, suitable heteroatoms will be apparent to those skilled in the art and include, for example, sulphur, nitrogen, oxygen, phosphorus and silicon. Particularly preferred is when the heteroatom is sulphur, nitrogen or oxygen, e.g. aziridine, tetrahydrofuran, pyrrolidine, pyrroline, piperidine, piperazine, thiazolidine, oxazolidine, morpholine, thiane, thiazine, pyrazolidine, pyrazoline, imidazolidine or imidazoline.

The term "alkoxy" refers to an O-alkyl group, wherein alkyl is as defined above. Preferably, the alkoxy group is a $C_{1-20}$ alkoxy group, more preferably a $C_{1-15}$ alkoxy group, more preferably still a $C_{1-10}$ alkoxy group, more preferably still a $C_{1-8}$ alkoxy group, more preferably still a $C_{1-6}$ alkoxy group. Particularly preferred alkoxy groups include, for example, methoxy, ethoxy, iso-propoxy, propoxy, butoxy, iso-butoxy, pentoxy and hexoxy.

Each of the alkyl, aryl, alkenyl, alkynyl, cycloalkyl, cycloalkenyl, heteroaryl, heterocycloalkyl and heterocycloalkenyl groups described herein may optionally be substituted by one or more substituents selected from alkyl, aryl, alkenyl, alkynyl, cycloalkyl, cycloalkenyl, heteroaryl, heterocycloalkyl, heterocycloalkenyl, halogen, nitro, cyano, silyl, sulfanyl, phosphanyl, hydroxy, alkoxy, amino, $CF_3$, amide, aminoalkyl, thiol, haloalkyl and haloalkoxy.

Preferably the one or more substituents are selected from, alkyl, halogen, nitro, cyano, hydroxy, alkoxy and amino. More preferably the one or more substituents are selected from $C_{1-6}$ alkyl, chlorine, bromine, nitro, cyano, hydroxy, $C_{1-6}$-alkoxy, $NH_2$, $NHC_{1-4}$-alkyl, and $N(C_{1-4}$-alkyl$)_2$. For example, methyl (Me), ethyl (Et), isopropyl (iPr), chlorine, nitro, hydroxy, MeO, EtO, iPrO, $NH_2$, NHMe, NHEt, $NMe_2$ and $NEt_2$.

Preferred substitution patterns of for example, when Rf is an aryl group are described hereinabove.

All publications mentioned in the above specification are herein incorporated by reference.

Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The following examples are intended to illustrate particular embodiments of the invention, and are not intended to limit the specification, including the claims in any manner.

EXAMPLES

Example 1a—Preparation of the Chiral Trans-Diamines

The preparation of the chiral trans-diamine of formula (1a) and (1b) may be represented by the reaction scheme A:

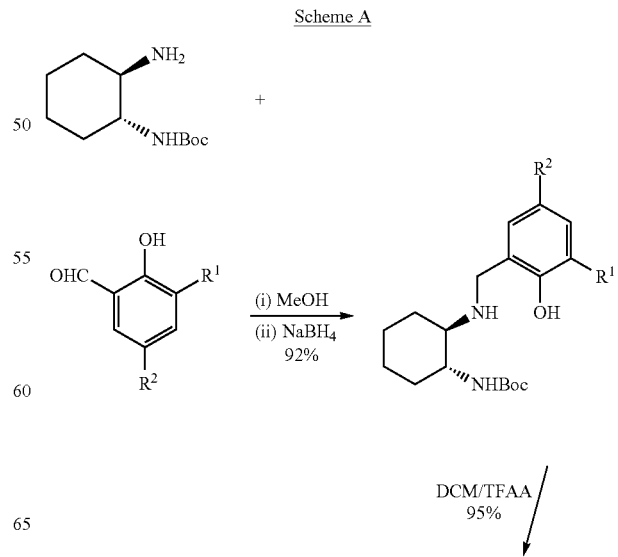

-continued

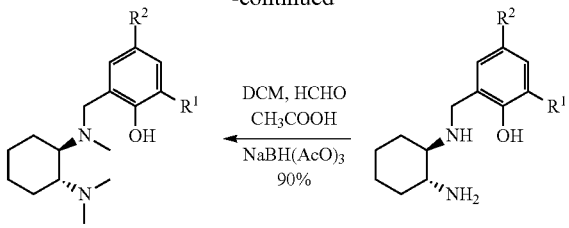

where R¹ is equivalent to Ri described hereinabove and R² is equivalent to Riii described hereinabove. For the ligand of formula (1a), R¹ and R² are both tert-butyl. For the ligand of formula (1b), R¹ is CF₃ and R² is hydrogen. The ligands of formula (1a) and (1b) have the following chemical structures:

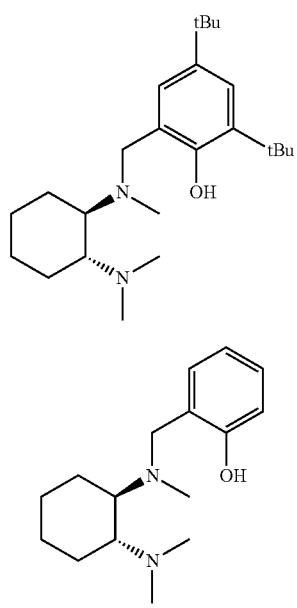

Both of the chiral trans-diamines of formula (1a) and (1b) were prepared from enantiomerically pure mono-BOC protected cyclohexane diamine in three steps (a) to (c).

Materials

Enantiomerically pure (>99% ee) (R,R) cyclohexane diamine was prepared according to the method disclosed in D. G. Gilheany (2003). The free amine was then protected with a mono-BOC protecting group as described in Viresh et al (2010). Salicylaldehyde was used directly, without purification.

Method steps (a) to (c) will now be described for the preparation of ligand (1a). These steps are, however, equally applicable to the preparation of ligand (1b) and ligands (1c) to (1k) (the chemical structures of which are shown below). The only difference is the substituents R¹ and R² on the phenyl ring.

Method Steps (a) to (c) for Ligand (1a)

(a) Preparation of tert-butyl N-[(1R,2R)-2-{[(3,5-di-tert-butyl-2-hydroxyphenyl)methyl]amino}cyclohexyl] carbamate Enantiomerically pure (>99% ee) (R,R) mono-BOC protected cyclohexane diamine (2.735 g, 12.8 mmol, 1.0 eq.) was dissolved in 25 ml of MeOH and 3,5-di-tertbutyl salicylaldehyde (2.99 g, 12.8 mmol, 1.0 eq.) was added in one portion. The mixture was agitated at room temperature for 5 hours (reaction followed by Thin Layer Chromatography) and NaBH₄ (2.6 g, 64.0 mmol, 5.0 eq.) was added slowly. Reaction was left stirring overnight, quenched with 100 ml of saturated NaHCO₃. Product was extracted ×3 with 100 ml of diethyl ether.

Organic phase was dried over sodium sulphate and the solvent was removed to yield 5.3 g of white solids (96% yield).

The white solid was then characterised by ¹H NMR.

¹H NMR (500 MHz, CDCl₃):

δ 7.21 (d, J=2.4, 1H), 6.84 (d, J=2.3, 1H), 4.42 (d, J=7.5, 1H), 4.07 (d, J=13.4, 1H), 3.89 (t, J=13.9, 1H), 3.39 (d, J=7.9, 1H), 2.28 (ddd, J=24.0, 15.3, 6.8, 2H), 2.08-1.94 (m, 1H), 1.72 (t, J=14.4, 2H), 1.46 (s, 9H), 1.42 (s, 9H), 1.31-1.25 (m, 9H), 1.23-1.10 (m, 4H).

(b) Preparation of 2-({[(1R,2R)-2-aminocyclohexyl]amino}methyl)-4,6-di-tert-butylphenol The tert-butyl N-[(1R,2R)-2-{[(3,5-di-tert-butyl-2-hydroxyphenyl) methyl] amino}cyclohexyl]carbamate from step (a) (5.3 g, 12.2 mmol, 1.0 eq.) was dissolved in 200 ml of ethyl acetate and 37% HCl (10 ml) was added. The mixture was agitated overnight, cooled to 0° C., quenched with saturated KOH solution (exothermic reaction) until the pH>12. Organic layer was extracted ×3 with 100 ml of diethyl ether, dried over sodium sulphate. Solvent was removed by vacuum to yield white foam (3.91 g, 92% yield).

The white foam was then characterised by ¹H NMR.

¹H NMR (500 MHz, CDCl₃):

δ 7.21 (d, J=2.3, 1H), 6.87 (d, J=2.2, 1H), 4.11-3.76 (m, 2H), 2.51-2.37 (m, 1H), 2.22-2.08 (m, 2H), 1.89 (dd, J=22.9, 15.7, 1H), 1.71 (dd, J=30.0, 14.5, 2H), 1.40 (d, J=20.2, 9H), 1.32-1.23 (m, 9H), 1.23-1.05 (m, 4H).

(c) Preparation of 2,4-di-tert-butyl-6-({[(1R,2R)-2-(dimethylamino)cyclohexyl](methyl)amino}methyl)phenol—Ligand of Formula (1a)

The 2-({[(1R,2R)-2-aminocyclohexyl]amino}methyl)-4,6-di-tert-butylphenol from step (b) (408 mg, 1.23 mmol, 1.0 eq) was dissolved in 15 ml of DCM and 37% HCHO (0.8 ml, excess) was added, followed by acetic acid (0.2 ml). The mixture was agitated at room temperature for 15 min, and sodium triacetoxyborohydride (1.6 g, 7.5 mmol, 6.0 eq.) was added in one portion. Reaction was stirred overnight, quenched by 100 ml of saturated NaHCO₃. The product was extracted ×3 with 50 ml of diethyl ether. Organic phase was washed ×3 with 100 ml of DIW, brine, dried over MgSO₄. Solvent was removed to yield 390 mg (86% Yield) of white foam.

The product was purified by flash chromatography using a cyclohexane:ethyl acetate ratio of 8:2) to yield a white crystalline solid.

Example 1b—Characterisation of the Chiral Trans-Diamines

Ligand (1a): 2,4-di-tert-butyl-6-({[(1R,2R)-2-(dimethylamino)cyclohexyl](methyl)amino}methyl) phenol The white crystalline solid obtained for the ligand of formula (1a) prepared according to scheme A above was characterised by ¹H and ¹³C NMR.

¹H NMR (400 MHz, CDCl₃):

δ 7.19 (d, J=2.3, 1H), 6.83 (d, J=2.2, 1H), 4.00-3.04 (m, 2H), 2.68-2.44 (m, 2H), 2.29 (d, J=27.8, 6H), 2.20 (s, 3H), 2.05-1.83 (m, 2H), 1.84-1.72 (m, 2H), 1.47-1.39 (m, 9H), 1.26 (d, J=13.5, 9H), 1.22-1.03 (m, 4H).

¹³C NMR (101 MHz, CDCl₃):

δ 154.5, 139.0, 135.3, 124.4, 123.1, 122.5, 64.0, 54.5, 39.3, 37.8, 35.0, 34.0, 31.8, 29.6, 26.9, 25.7, 25.6, 23.9, 22.1.

Ligand (1b): 2-((((1R,2R)-2-(Dimethylamino)cyclohexyl)(methyl)amino)methyl)-6-(trifluoromethyl)phenol The white crystalline solid obtained for the ligand of formula (1b) (790 mg, 65% purified yield) was characterised by ¹H and ¹³C NMR. Elemental analysis was also carried out using combustion analysis followed by quantitation by gas chromatography. This technique is known in the art.

¹H NMR (300 MHz, CDCl₃):

δ 7.43 (d, J=7.3 Hz, 1H), 7.13 (d, J=6.9 Hz, 1H), 6.72 (apparent t, J=7.2 Hz, 1H), 3.95 (d, J=12.7 Hz, 1H), 3.09 (broad, 1H), 2.80-2.43 (m, 2H), 2.30 (s, 6H), 2.21 (s, 3H), 2.15-1.91 (m, 2H), 1.91-1.73 (m, 2H), 1.39-1.09 (m, 4H).

¹³C NMR (101 MHz, CDCl₃):

δ 157.0, 133.5, 126.1, 125.9, 123.2, 117.8, 116.4, 64.3, 64.0, 51.6 (broad), 38.9 (broad), 26.9, 25.6, 23.4, 21.9; ¹⁹FMR (282 MHz, CDCl₃): δ −62.27 (s).

Elemental Analysis:

Calculated for $C_{17}H_{25}F_3N_2O$: C=61.80%, H=7.63%, N=8.48%.

Found: C=61.89%, H=7.56%, N=8.31%;

Melting point (M.p.)=117-119° C.

Ligand (1c): 2-(tert-Butyl)-6-((((1R,2R)-2-(dimethylamino)cyclohexyl)(methyl)amino)methyl)phenol

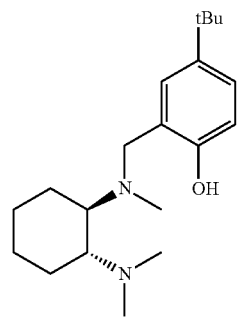

(1c)

Prepared from 196 mg of salicylaldehyde according to the preparation reaction scheme shown above as Scheme A. White, crystalline solid obtained (70 mg, 20% purified yield) with a melting point of 116-118° C.

¹H NMR (300 MHz, CDCl₃):

δ 7.18 (d, J=8.9 Hz, 1H), 6.87 (d, J=6.1 Hz, 1H), 6.66 (apparent t, J=8.9 Hz, 1H), 3.95 (d, J=12.4 Hz, 1H), 3.24 (broad, 1H), 2.71-2.48 (m, 2H), 2.29 (s, 6H), 2.22 (s, 3H), 2.03-1.84 (m, 2H), 1.83-1.72 (m, 2H), 1.44 (s, 9H), 1.40-1.18 (m, 4H).

¹³C NMR (101 MHz, CDCl₃):

δ 156.7, 136.4, 127.7, 125.5, 124.1, 117.0, 64.0, 63.8, 53.3 (broad), 38.6 (broad), 34.8, 29.5, 25.6, 24.7, 23.8, 22.0.

Elemental Analysis:

Calculated for $C_{20}H_{34}N_2O$: C=75.42%, H=10.76%, N=8.80%.

Found: C=74.95%, H=10.79%, N=8.43%.

Ligand (1d): 4-tert-Butyl-2-((((1R,2R)-2-(dimethylamino)cyclohexyl)methyl)amino)methyl)phenol (1d)

Prepared from 77 mg of salicylaldehyde according to the preparation reaction scheme shown above as Scheme A. White, crystalline solid obtained (85 mg, 62% purified yield).

¹H NMR (300 MHz, CDCl₃):

δ 7.08 (d, J=5.4 Hz, 1H), 6.90 (s, 1H), 6.70 (d, J=5.6 Hz, 1H), 3.80 (d, J=12.3 Hz, 1H), 3.03 (broad, 1H), 2.76-2.37 (m, 2H), 2.26 (s, 6H), 2.13 (s, 3H), 2.06-1.84 (m, 2H), 1.84-1.64 (m, 2H), 1.23 (s, 9H), 1.19-0.95 (m, 4H).

¹³C NMR (101 MHz, CDCl₃):

δ 155.2, 140.6, 126.7, 125.2, 123.3, 115.9, 64.6, 63.9, 52.0 (broad), 39.6 (broad), 37.8, 33.8, 31.6, 25.7, 25.6, 23.0, 21.7 ppm.

Elemental Analysis:

Calculated for $C_{20}H_{34}N_2O$: C=75.42%, H=10.76%, N=8.80%.

Found: C=75.12%, H=10.82%, N=8.56%.

Ligand (1e): 2-((((1R,2R)-2-(Dimethylamino)cyclohexyl)(methyl)amino)methyl)phenol

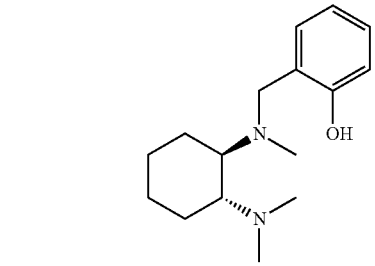

(1e)

Prepared from 270 mg of salicylaldehyde according to the preparation reaction scheme shown above as Scheme A. White powder obtained (377 mg, 65% purified yield).

¹H NMR (400 MHz, CDCl₃):

δ 7.17-7.10 (m, 1H), 7.00-6.93 (m, 1H), 6.86-6.80 (m, 1H), 6.74-6.66 (m, 1H), 3.95 (d, J=12.8 Hz, 1H), 3.08 (broad, 1H), 2.71-2.46 (m, 2H), 2.23 (s, 6H), 2.11 (s, 3H), 2.05-1.87 (m, 2H), 1.87-1.70 (m, 2H), 1.27-1.02 (m, 4H).

¹³C NMR (101 MHz, CDCl₃):
δ 156.7, 128.9, 127.6, 123.2, 117.0, 115.6, 63.5, 62.9, 50.7 (broad), 39.3 (broad), 37.5, 24.6, 24.5, 22.0, 20.7.

Ligand (1f): 2,4-Dichloro-6-((((1R,2R)-2-(dimethylamino)cyclohexyl)(methyl)amino)methyl)phenol

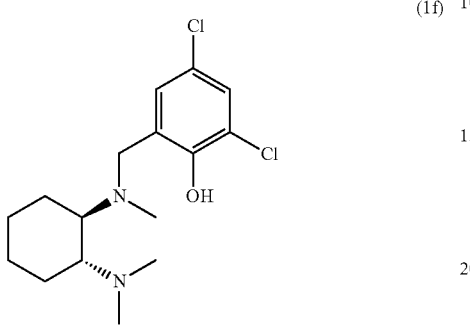

(1f)

Prepared from 159 mg of salicylaldehyde according to the preparation reaction scheme shown above as Scheme A. White crystalline solid obtained (190 mg, 69% purified yield).

¹H NMR (400 MHz, CDCl₃):
δ 7.22 (d, J=2.6 Hz, 1H), 6.85 (d, J=2.6 Hz, 1H), 3.82 (d, J=12.9 Hz, 1H), 2.95 (broad, 1H), 2.71-2.59 (m, 1H), 2.57-2.46 (m, 1H), 2.29 (s, 6H), 2.17 (s, 3H), 2.09-1.89 (m, 2H), 1.88-1.77 (m, 2H), 1.25-1.05 (m, 4H).

¹³C NMR (101 MHz, CDCl₃):
δ 153.2, 128.4, 128.2, 127.1, 122.1, 121.3, 64.5, 63.9, 51.7 (broad), 38.8 (broad), 25.5, 25.5, 23.1, 21.9.

High Resolution Mass Spectrometry (HRMS) [Electron Spray Ionisation (ESI)] (M+H):
Calculated for $C_{16}H_{25}Cl_2N_2O$: 331.1344. Found: 331.1351.

Ligand (1g): 2-((((1R,2R)-2-(Dimethylamino)cyclohexyl)(methyl)amino)methyl)-6-methoxyphenol

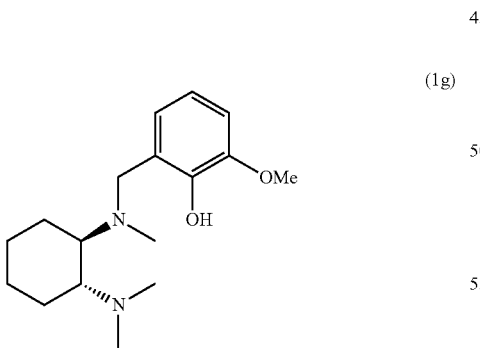

(1g)

Prepared from 147 mg of salicylaldehyde according to the preparation reaction scheme shown above as Scheme A. White powder obtained (76 mg, 28% purified yield).

¹H NMR (400 MHz, CDCl₃):
δ 6.83-6.76 (m, 1H), 6.72 (t, J=7.7 Hz, 1H), 6.62-6.57 (m, 1H), 3.92 (d, J=12.8 Hz, 1H), 3.86 (s, 3H), 3.11 (d, J=12.8 Hz, 1H), 2.72-2.43 (m, 2H), 2.32 (s, 3H), 2.17 (s, 3H), 2.05-1.88 (m, 2H), 1.87-1.75 (m, 2H), 1.25-1.09 (m, 4H).

¹³C NMR (101 MHz, CDCl₃):
δ 148.3, 147.0, 124.5, 122.1, 117.5, 110.6, 64.5, 56.1, 55.8, 52.3 (broad), 38.3 (broad), 25.6, 25.6, 25.3, 23.0, 21.7.
HRMS (ESI) (M+H):
Calculated for $C_{17}H_{29}N_2O_2$: 293.2150. Found: 293.2143.

Ligand (1h): 2-(Adamantan-1-yl)-4-tert-butyl-6-((((1R,2R)-2-(dimethylamino)cyclohexyl)(methyl)amino)methyl)phenol

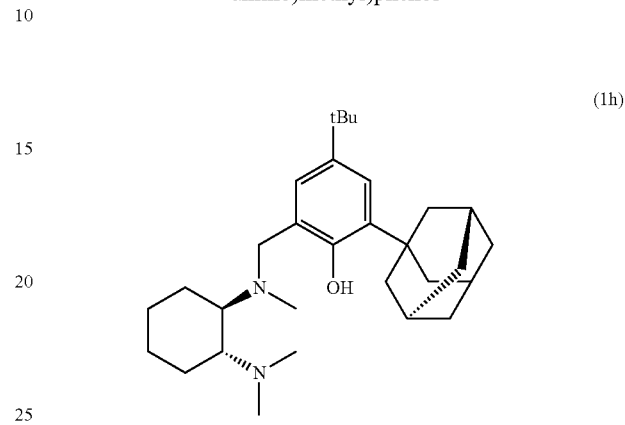

(1h)

Prepared from 192 mg of salicylaldehyde according to the preparation reaction scheme shown above as Scheme A. White solid obtained (53 mg, 19% purified yield).

¹H NMR (300 MHz, CDCl₃):
δ 7.16 (d, J=2.0 Hz, 1H), 6.86 (d, J=1.9 Hz, 1H), 3.96 (d, J=12.8 Hz, 1H), 3.12 (broad, 1H), 2.70-2.43 (m, 2H), 2.29 (s, 6H), 2.26 (s, 3H), 2.25 (s, 5H), 2.07 (broad, 4H), 2.05-1.89 (m, 2H), 1.82 (s, 8H), 1.25 (s, 9H), 1.29-1.12 (m, 4H).

HRMS (ESI (M+H): calculated for $C_{30}H_{49}N_2O$: 453.3766. Found: 453.3752.

Ligand (1i): 4-Bromo-2-tert-butyl-6-((((1R,2R)-2-(dimethylamino)cyclohexyl)(methyl)amino) methyl) phenol

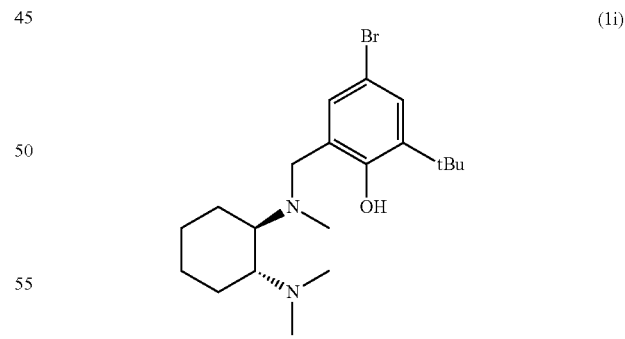

(1i)

Prepared from 304 mg of salicylaldehyde according to the preparation reaction scheme shown above as Scheme A. White solid obtained (320 mg, 68% purified yield) with a melting point of 112-114° C.

¹H NMR (300 MHz, CDCl₃):
δ 7.26 (s, 1H), 6.98 (s, 1H), 3.89 (d, J=12.6 Hz, 1H), 3.10 (broad, 1H), 2.75-2.51 (m, 2H), 2.28 (s, 6H), 2.20 (s, 3H), 2.08-1.85 (m, 2H), 1.85-1.77 (m, 2H), 1.41 (s, 9H), 1.38-1.18 (m, 4H).

$^{13}$C NMR (101 MHz, CDCl$_3$):

δ 156.2, 138.9, 130.0, 128.5, 127.4, 109.1, 63.9, 63.7, 52.4 (broad), 38.7 (broad), 35.0, 29.3, 25.6, 23.7, 22.1, 22.0.

Elemental Analysis:

Calculated for C$_{20}$H$_{33}$BrN$_2$O: C=60.45%, H=8.37%, N=7.05%.

Found: C=60.26%, H=8.3%, N=6.76%.

Ligand (1j): 2-tert-Butyl-6-((((1R,2R)-2-(dimethylamino)cyclohexyl)(methyl)amino) methyl)-4-nitrophenol

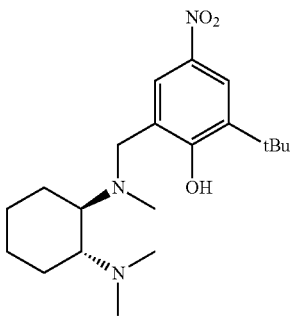

(1j)

Prepared from 461 mg of salicylaldehyde according to the preparation reaction scheme shown above as Scheme A. Yellow powder obtained (210 mg, 28% purified yield).

$^1$H NMR (400 MHz, CDCl$_3$):

δ 8.12 (d, J=2.9 Hz, 1H), 7.84 (d, J=2.8 Hz, 1H), 3.93 (d, J=12.9 Hz, 1H), 2.99 (broad, 1H), 2.77 (broad, 1H), 2.65-2.41 (m, 2H), 2.34 (s, 6H), 2.21 (s, 3H), 2.10-1.92 (m, 2H), 1.92-1.81 (m, 2H), 1.43 (s, 9H), 1.29-1.15 (m, 4H).

$^{13}$C NMR (101 MHz, CDCl$_3$):

δ 166.1, 137.7, 136.9, 128.1, 124.6, 122.8, 64.0, 62.7, 51.3 (broad), 39.2 (broad), 39.0, 36.2, 31.9, 29.2, 25.4, 23.3, 22.3.

Elemental Analysis:

Calculated for C$_{20}$H$_{33}$N$_3$O$_3$: C=66.08%, H=9.15%, N=11.56%.

Found: C=65.60%, H=9.03%, N=11.20%.

Ligand (1k): 2-tert-Butyl-4-(dimethylamino)-6-((((1R,2R)-2-(dimethylamino)cyclohexyl)(methyl)amino)methyl)phenol

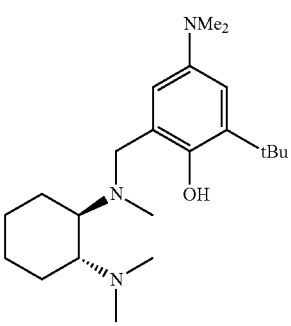

(1k)

Prepared from 223 mg of salicylaldehyde according to the preparation reaction scheme shown above as Scheme A. Yellow crystalline solid obtained (60 mg, 16% purified yield).

$^1$H NMR (400 MHz, CDCl$_3$):

δ 6.74 (d, J=3.0 Hz, 1H), 6.38 (d, J=3.0 Hz, 1H), 3.91 (d, J=12.7 Hz, 1H), 3.22 (broad, 1H), 2.80 (s, 6H), 2.66-2.47 (m, 2H), 2.24 (s, 6H), 2.20 (s, 3H), 2.01-1.84 (m, 2H), 1.84-1.74 (m, 2H), 1.41 (s, 9H), 1.26-1.09 (m, 4H).

$^{13}$C NMR (101 MHz, CDCl$_3$):

δ 149.9, 149.8, 142.9, 136.7, 115.4, 113.4, 64.0, 56.3 (broad), 47.3 (broad), 43.2, 42.7, 35.1, 29.5, 25.7, 25.6, 24.1, 22.0.

HRMS (ESI) (M+H):

Calculated for C$_{22}$H$_{40}$N$_3$O: 362.3171.

Found: 362.3158.

Comparative Ligand (1l): (1R,2R)—N$^1$-(3,5-di-tert-Butyl-2-methoxybenzyl)-N$^1$,N$^2$,N$^2$-trimethylcyclohexane-1,2-diamine

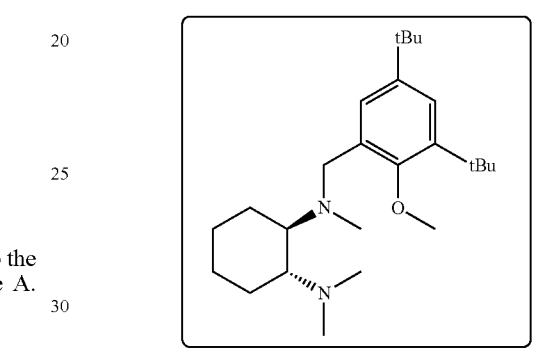

(1l)

Prepared from 605 mg of 3,5-di-tert-butyl-2-methoxybenzaldehyde. White powder obtained (540 mg, 57% yield).

$^1$H NMR (300 MHz, CDCl$_3$):

δ 7.51 (d, J=2.5 Hz, 1H), 7.23 (d, J=2.5 Hz, 1H), 3.79 (d, J=13.2 Hz, 1H), 3.78 (s, 3H), 3.77 (d, J=13.2 Hz, 1H), 2.66-2.41 (m, 2H), 2.32 (s, 6H), 2.26 (s, 3H), 2.05-1.80 (m, 2H), 1.80-1.65 (m, 2H), 1.41 (s, 9H), 1.30 (s, 9H), 1.27-1.06 (m, 4H).

Example 2—General Procedure for Addition of Grignard Reagents to Ketones in Presence of Chiral Ligand of Formula (1)

The general procedure followed for the preparation of a chiral alcohol in the presence of chiral ligand of formula (1) was as follows:

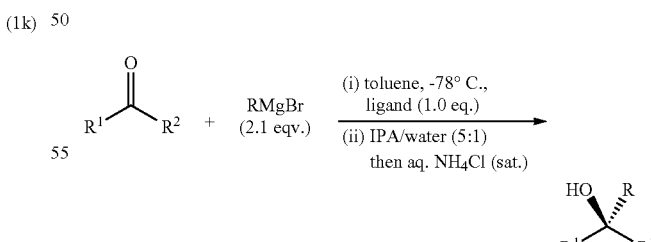

Ligand 1 (38 mg, 0.1 mmol, 1.0 eq.) and a ketone (0.1 mmol, 1.0 eq.) were dissolved in 0.75 mL of dry toluene under nitrogen atmosphere and cooled to −78° C. A Grignard reagent in toluene/ether 6:1, 0.43M (0.21 mmol, 2.1 eq.) was added slowly dropwise. The mixture was agitated at −78° C. and monitored by HPLC (GC) until no more product formation was detected. The reaction was quenched by addition of isopropyl alcohol (IPA)/water (2 mL), followed by saturated NH₄Cl (2 mL) and heptane (2 mL) and mixture was allowed to heat to room temperature. The aqueous layer was separated and extracted with heptane (3×5 mL). The organic phases were combined, washed with 20% aqueous solution of acetic acid (3×5 mL), water (3×5 mL), brine (5 mL) and dried over anhydrous Na₂SO₄. The solvent was removed by rotary evaporator. The crude product was purified by flash chromatography using EtOAc/cyclohexane mixture as eluent.

In order to recover the ligand, the aqueous phases from the above reaction work-up were combined, washed with toluene (3×5 mL) and basified to pH>9 with aqueous 5M NaOH. The recovered ligand was extracted by toluene (3×5 mL). The organic phase was washed with water (3×5 mL), brine (1×5 mL) and dried over anhydrous Na₂SO₄. The solvent was removed by vacuum. The ligand was then purified by recrystallization from hot IPA/water to provide an 80% yield.

Example 3—Preparation of Chiral Alcohols Using the Ligand of Formula (1a)

a) 2-phenyl-2-butanol (Compound of Formula 3a)

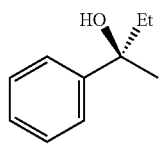

3a

Ligand 1a (38 mg, 0.1 mmol, 1.0 eq.) was dissolved in 0.5 ml of dry toluene and 0.25 ml of 0.4M acetophenone in dry toluene was added. The mixture was cooled to −78° C. 0.07 ml of ethyl magnesium bromide (3M in ether) was diluted to 0.5 ml with dry toluene and added slowly dropwise over 30 minutes. The mixture was agitated at −78° C. for 1 hour and quenched by addition of IPA/water (2 mL), followed by saturated NH₄Cl (2 mL) and heptane (2 mL). The mixture was allowed to heat to room temperature. The aqueous layer was separated and extracted with heptane (3×5 mL). The organic phases were combined, washed with 20% aqueous solution of acetic acid (3×5 mL), water (3×5 mL), brine (5 mL) and dried over anhydrous Na₂SO₄. The solvent was removed by rotary evaporator.

The crude product was purified by flash chromatography using EtOAc/cyclohexane mixture as eluent to yield 11.5 mg (77% yield) of 2-phenyl-2-butanol (compound of formula 3a).

The product was then characterised by $^1$H NMR and the enantiomeric excess was calculated according to the method described below.

$^1$H NMR (CDCl₃):

δ 0.81 (3H, t), 1.55 (3H, s), 2.06 (2H, m), 7.24 (1H, t), 7.34 (2H, dd, J=7.7), 7.44 (2H, t)

b) 1-ethyl-2,3-dihydro-1H-Inden-1-ol (Compound of Formula 3g)

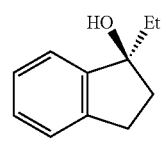 [SMILES: CC[C@]1(O)CCc2ccccc21]

3g

Ligand 1a (1.89 g, 5 mmol, 1.0 eq.) of was dissolved in 25 ml of dry toluene and 12.5 ml of 0.4M acetophenone in dry toluene was added. The mixture was cooled to −78° C. 3.5 ml of ethyl magnesium bromide (3M in ether) was diluted to 20 ml with dry toluene and added slowly dropwise over 60 minutes and the mixture was agitated at −78° C. for 3 h. The reaction was quenched by addition of IPA/water (100 mL), followed by saturated NH₄Cl (100 mL) and heptane (100 mL) and allowed to heat to room temperature. The aqueous layer was separated and extracted with heptane (3×100 mL). Organic phases were combined, washed with 20% aqueous solution of acetic acid (3×100 mL), water (3×100 mL), brine (100 mL) and dried over anhydrous Na₂SO₄. The solvent was removed by rotary evaporator.

The crude product was purified by flash chromatography using EtOAc/cyclohexane mixture as eluent to yield 801 mg (99% yield) of 1-ethyl-2,3-dihydro-1H-inden-1-ol.

The product was then characterised by $^1$H NMR and the enantiomeric excess was calculated according to the method described below.

$^1$H NMR (CDCl₃):

δ 1.01 (3H, t), 1.81 (1H, m), 1.92 (1H, m), 2.05 (1H, m), 2.30 (1H, m), 2.82 (1H, m), 3.02 (1H, m), 7.21 (3H, m), 7.31 (1H, m)

Analysis of Enantiomeric Excess

The produced chiral alcohols were analysed by high performance liquid chromatography on chiral stationary phases (CSP-HPLC). Typically a 25 μL sample of the reaction mixture was injected onto the HPLC column at 1 ml/min flow rate and detected simultaneously at 210 nm, 230 nm and 254 nm.

2-phenyl-2-butanol (3a) was analysed on a CHIRAL OJ-H column with n-heptane/ethanol (95:05) as the mobile phase. This gave an enantiomeric excess of 80% and retention times of 13.7 min (major) and 11.8 min (minor) for the two enantiomers.

1-ethyl-2,3-dihydro-1H-inden-1-ol (3g) was analysed on a CHIRAL OJ-H column with n-heptane/ethanol (96:04) as the mobile phase. This gave an enantiomeric excess of 90% and retention times of 11.95 min (major) and 11.20 min (minor) for the two enantiomers.

After recrystallization, the product had an enantiomeric excess of greater than 99%. In other words, a substantially enantiopure product was obtained.

Example 4—Effect of First Reactant on Stereoselectivity and Yield

In the presence of the ligand 1a, the reaction of p-methoxy acetophenone with ethyl magnesium chloride in diethyl ether/toluene mixture at −78° C. according to the general procedure described in Example 2 produced the chiral alcohol product of formula 3b with a modest 36% ee.

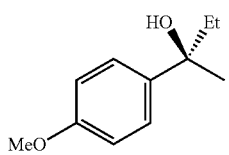

3b

By changing the halide in the Grignard reagent to bromide (ethyl magnesium bromide), the enantioselectivity was increased to 66%. The method was then optimised further by altering the order of addition, and the concentration of the reactants to obtain 73% ee in 53% yield. The method was, for example, optimised by adding the Grignard reagent to a mixture of ketone and ligand.

The method can be represented generally by the following reaction scheme:

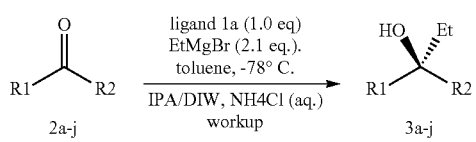

A series of chiral alcohols (3a-j) were then prepared to determine the effect of the ketone substituents (2a-2j) on the enantioselectivity and yield. In all cases, reactions were performed according to the above reaction scheme.

The results are shown in Table 1a below.

TABLE 1a

| 3a-3j | Product | Time (hours) | Yield (%)[a] | ee [%][b] |
|---|---|---|---|---|
| 3a | (structure) | 1 | 77 | 80 |
| 3b | (structure) | 1 | 53 | 73 |
| 3c | (structure) | 1 | 99 | 54 |
| 3d | (structure) | 2 | 57 | 93 |
| 3e | (structure) | 2 | 71 | 30 |

TABLE 1a-continued

| 3a-3j | Product | Time (hours) | Yield (%)[a] | ee [%][b] |
|---|---|---|---|---|
| 3f | (structure) | 2 | 73 | 91 |
| 3g | (structure) | 3 | 99 | 90 |
| 3h | (structure) | 2 | 45 | 93 |
| 3i | (structure) | 1 | | |
| 3j | (structure) | 1 | | |

[a] 3a and 3g were isolated yields. 3b to 3d and 3h to 3j were NMR yields measured by applying an internal standard (ligand) 1a used as the internal standard, 400 MHz (CDCl₃). Chiral phase HPLC was also used and the same/similar yields were obtained.
b measured by chiral phase HPLC Further chiral alcohols 3k and 3l were also prepared following the same reaction scheme as for chiral alcohols 3a to 3j. The enantioselectivity and yield obtained are shown in Table 1b below.

TABLE 1b

| 3k-3l | Product | Yield (%)[a] | ee [%][b] |
|---|---|---|---|
| 3k | | 71 | 60 |
| 3l | | 51 | 50 |

[a] Yields measured by chiral phase HPLC
[b] measured by chiral phase HPLC

Analysis of Enantiomeric Excess

The produced chiral alcohols were analysed by high performance liquid chromatography on chiral stationary phases (CSP-HPLC). Typically a 25 μL sample of the reaction mixture was injected onto the HPLC column at 1 ml/min flow rate and detected simultaneously at 210 nm, 230 nm and 254 nm.

For example:

2-(4-methoxyphenyl)butan-2-ol (3b) was analysed on a CHIRAL IB column with n-heptane/ethanol (99.5:0.5) as the mobile phase. This gave an enantiomeric excess of 73% and retention times of 20.27 min (major) and 19.24 min (minor) for the two enantiomers.

2-(4-(trifluoromethyl)phenyl)butan-2-ol (3c) was analysed on a CHIRAL OJ-H column with n-heptane/ethanol (99:01) as the mobile phase. This gave an enantiomeric excess of 54% and retention times of 14.21 min (major) and 13.09 min (minor) for the two enantiomers.

1-ethyl-1,2,3,4-tetrahydronaphthalen-1-ol (3d) was analysed on a CHIRAL IA column with n-heptane/ethanol (99:01) as the mobile phase. This gave an enantiomeric excess of 93% and retention times of 24.69 min (major) and 19.80 min (minor) for the two enantiomers.

2-ethyl-1,2,3,4-tetrahydronaphthalen-1-ol (3e) was analysed on a CHIRAL IA column with n-heptane/ethanol (97:03) as the mobile phase. This gave an enantiomeric excess of 30% and retention times of 15.21 min (major) and 10.54 min (minor) for the two enantiomers.

5-ethyl-6,7,8,9-tetrahydro-5H-benzo[7]annulen-5-ol (3f) was analysed on a CHIRAL OJ-H column with n-heptane/ethanol (96:04) as the mobile phase. This gave an enantiomeric excess of 91% and retention times of 11.12 min (major) and 10.22 min (minor) for the two enantiomers.

4-ethyl-chroman-4-ol (3h) was analysed on a CHIRAL OJ-H column with n-heptane/ethanol (97:03) as the mobile phase. This gave an enantiomeric excess of 93% and retention times of 23.26 min (major) and 14.62 min (minor) for the two enantiomers.

Comments

Although the best enantioselectivities were obtained for a range of cyclic alkyl-aryl ketones (>93% ee for compounds of formula 3d and 3h), the system was also found to transmit stereochemical information for alkyl-alkyl and alkyl-aryl ketones with moderate to high ee's. The relative decrease in enantioselectivity between 3a and 3c was possibly caused by an increased electropositivity of the carbonyl carbon atom influenced by the strongly electron withdrawing group, leading to a faster reaction.

Example 5—Effect of the Grignard Reagent on Stereoselectivity and Yield

The effect of the Grignard reagents was then investigated. Taking the ketone of formula 2g, the nature of the Grignard reagent was varied according to the following reaction scheme:

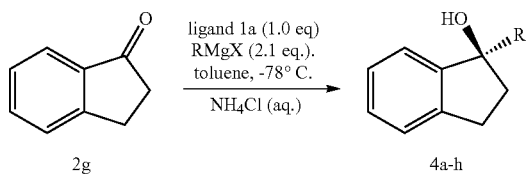

A series of chiral alcohols (4a-h) were prepared to determine the effect of the Grignard reagent on the enantioselectivity, yield and competing reduction pathway. In all cases, reactions were performed according to the above reaction scheme. The competing reaction pathway is the formation of the reduction product and may be represented as follows:

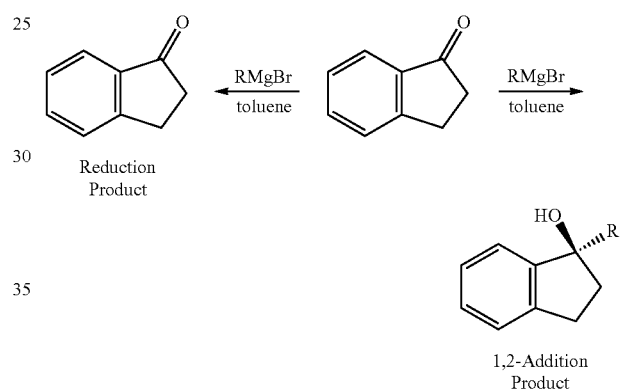

The results are shown in Table 2a below.

TABLE 2a

| 4a-4j | Grignard | Product | Time (hours) | Reduced product [%] | Yield (%)[a] | ee [%][b] |
|---|---|---|---|---|---|---|
| 4a | MeMgBr | HO,,,Me (indane) | 1 | — | 86 | 77 |
| 4b | MeMgI | HO,,,Me (indane) | 1 | — | 51 | 90 |
| 4c | | HO,,,allyl (indane) | 1 | — | 97 | 20 |

TABLE 2a-continued

| 4a-4j | Grignard | Product | Time (hours) | Reduced product [%] | Yield (%)[a] | ee [%][b] |
|---|---|---|---|---|---|---|
| 4d | | (1-cyclopentyl-2,3-dihydro-1H-inden-1-ol) | 1 | 1% (94%[c]) | 80 | 79 |
| 4e | | (1-isobutyl-2,3-dihydro-1H-inden-1-ol) | 1 | 1% (65%[c]) | 49 | 85 |
| 4f | | (1-phenyl-2,3-dihydro-1H-inden-1-ol) | 1 | 0 | 31 | 28 |
| 4g | EtMgI | (1-ethyl-2,3-dihydro-1H-inden-1-ol) | 1 | 0 | 99 | 94 |
| 4h | | (1-o-tolyl-2,3-dihydro-1H-inden-1-ol) | 1 | 0 | 36 | 33 | a NMR yields measured by applying an internal standard (ligand 1a used as the internal standard), 400 MHz (CDCl$_3$)
b measured by chiral phase HPLC
c formed without the presence of a ligand Analysis of Enantiomeric Excess The produced chiral alcohols were analysed by high performance liquid chromatography on chiral stationary phases (CSP-HPLC). Typically a 25 μL sample of the reaction mixture was injected onto the HPLC column at 1 ml/min flow rate and detected simultaneously at 210 nm, 230 nm and 254 nm.

For example:

Methyl-2,3-dihydro-1H-inden-1-ol (4a) was analysed on a CHIRAL IB column with n-heptane/ethanol (96:04) as the mobile phase. This gave an enantiomeric excess of 77% and retention times of 6.38 min (major) and 6.11 min (minor) for the two enantiomers.

1-cyclopentyl-2,3-dihydro-1H-inden-1-ol (4d) was analysed on a CHIRAL OJ-H column with n-heptane/ethanol (96:04) as the mobile phase. This gave an enantiomeric excess of 79% and retention times of 12.77 min (major) and 10.87 min (minor) for the two enantiomers.

1-isobutyl-2,3-dihydro-1H-inden-1-ol (4e) was analysed on a CHIRAL IA column with n-heptane/ethanol (96:04) as the mobile phase. This gave an enantiomeric excess of 85% and retention times of 11.08 min (major) and 9.19 min (minor) for the two enantiomers.

1-phenyl-2,3-dihydro-1H-inden-1-ol (4l) was analysed on a CHIRAL OJ-H column with n-heptane/ethanol (93:07) as the mobile phase. This gave an enantiomeric excess of 28% and retention times of 21.64 min (major) and 18.47 min (minor) for the two enantiomers.

1-phenyl-1-o-tolylethanol (4h) was analysed on a CHIRAL OJ-H column with n-heptane/ethanol (95:05) as the mobile phase. This gave an enantiomeric excess of 33% and retention times of 15.66 min (major) and 20.73 min (minor) for the two enantiomers.

Comments

It can be seen from Table 2a that the system was found to be generally applicable with respect to alkyl magnesium halides, and resulted in slightly lower stereoselectivities for aryl magnesium halides. Methylmagnesium bromide for example, produced an 86% yield and a 77% enantiomeric excess whereas phenylmagnesium bromide produced a 31% yield and 28% enantiomeric excess.

The results, however, demonstrate unprecedentedly high ee values for small alkyl unbranched Grignard reagents. Methyl 4b and ethyl 4g magnesium iodide give rise to enantiomeric excesses of 90% and 94% respectively.

It was also observed that in the absence of ligand 1a, branched Grignard reagents 4d and 4e yielded 94% and 65% of reduced secondary alcohol product when added to 1-indanone under the same conditions. Also in case of 4d and 4e, 1,2-addition products were not formed at all (0% for 4d) or in small quantity (4% for 4e). Interestingly therefore, it appears that the addition of 1.0 eq. of ligand 1a disturbed the balance between rates of enolisation, reduction and 1,2-addition in favour of addition products. Only a trace of 1-indanol was found in the reaction mixture after the quench of the reaction (1%) and a yield of the tertiary alcohol 4d increased to 80% and 4e to 49%.

It can be seen from comparing the yields and the enantiomeric excess obtained with Grignard reagents 4a and 4b (yields of 86% and 51%; enantiomeric excess of 77% and 90%) that the halide ion of the Grignard reagent appears to have an effect on the reaction. This effect was therefore investigated further by carrying out the following reaction with ligand (1a) and either ethylmagnesium bromide (R=ethyl; X=Br) or ethylmagnesium iodide (R=ethyl; X=I).

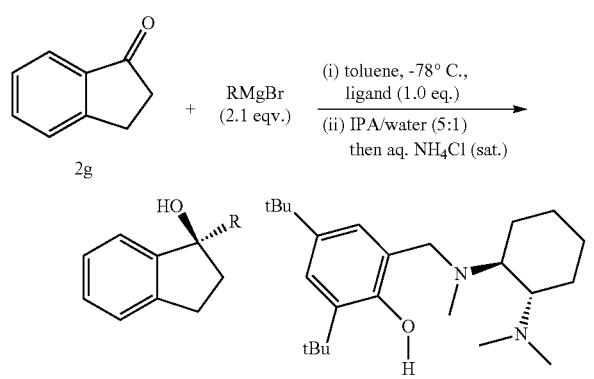

Ethylmagnesium bromide gave rise to an enantiomeric excess of 90%, whereas ethylmagnesium iodide increased the enantiomeric excess to 94%.

Further studies on Grignard reagents were also carried out according to the following reaction scheme:

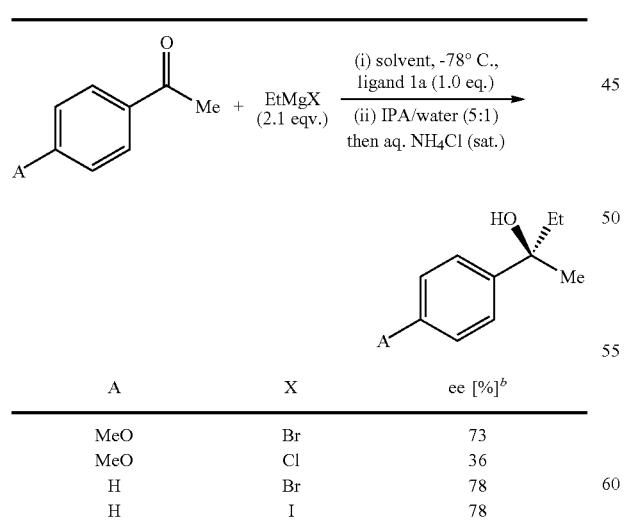

| A | X | ee [%][b] |
|---|---|---|
| MeO | Br | 73 |
| MeO | Cl | 36 |
| H | Br | 78 |
| H | I | 78 |

[b]measured by chiral HPLC

To further investigate the effect of the "R" group in the Grignard reagent, reactions were carried out according to the following scheme:

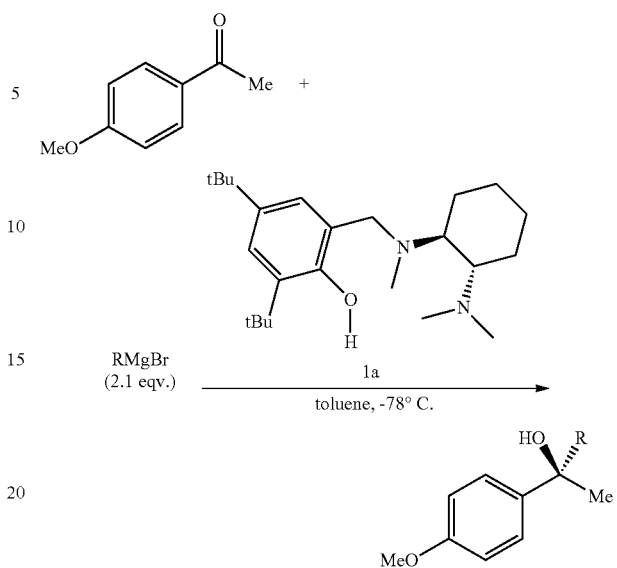

A series of chiral alcohols (4i-4p) were prepared to determine the effect of the "R" group on the enantioselectivity. The results are shown below in Table 2b.

TABLE 2b

| 4i-4p | Product | ee [%][b] |
|---|---|---|
| 4i |  | 73 |
| 4j |  | 78 |
| 4k |  | 72 |
| 4l |  | 76 |

TABLE 2b-continued

| 4i-4p | Product | ee [%][b] |
|---|---|---|
| 4m | 2-(4-methoxyphenyl)pentan-2-ol structure | 68 |
| 4n | 2-(4-methoxyphenyl)-4-phenylbut-3-yn-2-ol structure | 44 |
| 4o | 1-(4-methoxyphenyl)-1-(naphthalen-2-yl)ethanol structure | 58 |
| 4p | 1-(4-methoxyphenyl)-1-(naphthalen-1-yl)ethanol structure | 52 | b measured by chiral phase HPLC

Analysis of Enantiomeric Excess

The produced chiral alcohols were analysed by high performance liquid chromatography on chiral stationary phases (CSP-HPLC). Typically a 25 µL sample of the reaction mixture was injected onto the HPLC column at 1 ml/min flow rate and detected simultaneously at 210 nm, 230 nm and 254 nm.

For example:

2-(4-methoxyphenyl)-3-methylbutan-2-ol (4j) was analysed on a CHIRAL IB column with n-heptane/ethanol (97:03) as the mobile phase. This gave an enantiomeric excess of 78% and retention times of 7.13 min (major) and 6.70 min (minor) for the two enantiomers.

1-cyclopentyl-1-(4-methoxyphenyl)ethanol (4l) was analysed on a CHIRAL IA column with n-heptane/ethanol (97:03) as the mobile phase. This gave an enantiomeric excess of 76% and retention times of 17.45 min (major) and 24.39 min (minor) for the two enantiomers.

2-(4-methoxyphenyl)pentan-2-ol (4m) was analysed on a CHIRAL IA column with n-heptane/ethanol (90:10) as the mobile phase. This gave an enantiomeric excess of 68% and retention times of 8.10 min (major) and 8.50 min (minor) for the two enantiomers.

2-(4-methoxyphenyl)-4-phenylbut-3-yn-2-ol (4n) was analysed on a CHIRAL IC column with n-heptane/ethanol (97:03) as the mobile phase. This gave an enantiomeric excess of 44% and retention times of 10.23 min (major) and 11.04 min (minor) for the two enantiomers.

1-(4-methoxyphenyl)-1-(naphthalen-1-yl)ethanol (4o) was analysed on a CHIRAL IA column with n-heptane/ethanol (95:05) as the mobile phase. This gave an enantiomeric excess of 58% and retention times of 11.82 min (major) and 13.97 min (minor) for the two enantiomers.

1-(4-methoxyphenyl)-1-(naphthalen-2-yl)ethanol (4p) was analysed on a CHIRAL IA column with n-heptane/ethanol (95:05) as the mobile phase. This gave an enantiomeric excess of 52% and retention times of 18.46 min (major) and 23.60 min (minor) for the two enantiomers.

Comments

It can be seen that the system is generally applicable to alkyl, cycloalkyl, alkenyl, and aryl magnesium bromide Grignard reagents, although lower stereoselectivities are seen with alkenyl and aryl magnesium bromides.

Further studies were also carried out to determine the effect of substituents on the enantioselectivity obtained with aryl Grignard reagents. The studies were conducted according to the following reaction scheme:

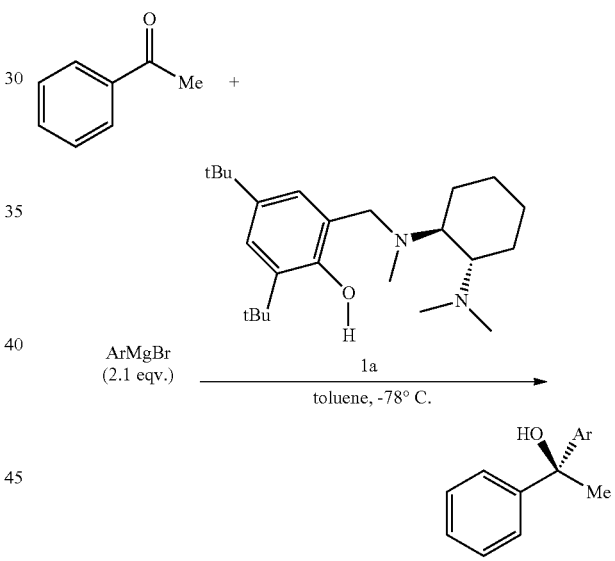

A series of chiral alcohols were prepared and the results are shown below in Table 2c.

TABLE 2c

| 4q-4w | Product | ee [%][b] |
|---|---|---|
| 4q | 1-phenyl-1-(2-methylphenyl)ethanol structure | 33 |

TABLE 2c-continued

| 4q-4w | Product | ee [%][b] |
|---|---|---|
| 4r | | 20 |
| 4s | | 51 |
| 4t | | 75 |
| 4u | | 51 |
| 4v | | 55 |
| 4w | | 55 |
| 4x | | 47 |
| 4y | | 44 |

[b] measured by chiral phase HPLC

Analysis of Enantiomeric Excess

The produced chiral alcohols were analysed by high performance liquid chromatography on chiral stationary phases (CSP-HPLC). Typically a 25 μL sample of the reaction mixture was injected onto the HPLC column at 1 ml/min flow rate and detected simultaneously at 210 nm, 230 nm and 254 nm.

For example:

1-(2,3-dichlorophenyl)-1-phenylethanol (4r) was analysed on a CHIRAL IB column with n-heptane/ethanol (95:05) as the mobile phase. This gave an enantiomeric excess of 20% and retention times of 6.581 min (major) and 7.389 min (minor) for the two enantiomers.

1-(3,4-dichlorophenyl)-1-phenylethanol (4s) was analysed on a CHIRAL OJ-H column with n-heptane/ethanol (95:05) as the mobile phase. This gave an enantiomeric excess of 51% and retention times of 13.333 min (major) and 15.837 min (minor) for the two enantiomers.

1-(naphthalen-1-yl)-1-phenylethanol (4t) was analysed on a CHIRAL IA column with n-heptane/ethanol (97:03) as the mobile phase. This gave an enantiomeric excess of 75% and retention times of 9.800 min (major) and 11.029 min (minor) for the two enantiomers.

1-(3,5-dimethylphenyl)-1-phenylethanol (4u) was analysed on a CHIRAL IB column with n-heptane/ethanol (99:01) as the mobile phase. This gave an enantiomeric excess of 51% and retention times of 9.237 min (major) and 10.191 min (minor) for the two enantiomers.

1-phenyl-1-(4-trifluoromethyl)phenyl)ethanol (4v) was analysed on a CHIRAL IA column with n-heptane/ethanol (95:05) as the mobile phase. This gave an enantiomeric excess of 55% and retention times of 9.274 min (major) and 7.808 min (minor) for the two enantiomers.

1-phenyl-1-(3-(trifluoromethyl)phenyl)ethanol (4w) was analysed on a CHIRAL OJ-H column with n-heptane/ethanol (95:05) as the mobile phase. This gave an enantiomeric excess of 55% and retention times of 10.098 min (major) and 12.433 min (minor) for the two enantiomers.

1-(3-bromophenyl)-1-phenylethanol (4x) was analysed on a CHIRAL IA column with n-heptane/ethanol (99:01) as the mobile phase. This gave an enantiomeric excess of 47% and retention times of 17.774 min (major) and 23.433 min (minor) for the two enantiomers.

1-(3-methoxyphenyl)-1-phenylethanol (4y) was analysed on a CHIRAL IB column with n-heptane/ethanol (97:03) as the mobile phase. This gave an enantiomeric excess of 44% and retention times of 10.580 min (major) and 11.264 min (minor) for the two enantiomers.

Comments

It can be seen from Table 2c that the system is generally applicable to a wide range of substituted aryl Grignard reagents.

An unexpectedly high enantiomeric excess of 75% was obtained with 1-naphthylmagnesium bromide (4t).

Example 6—Further Studies with Chiral Ligand (1a)

Further substrate studies were conducted with ligand (1a). The general reaction can be represented as follows:

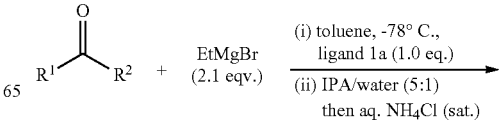

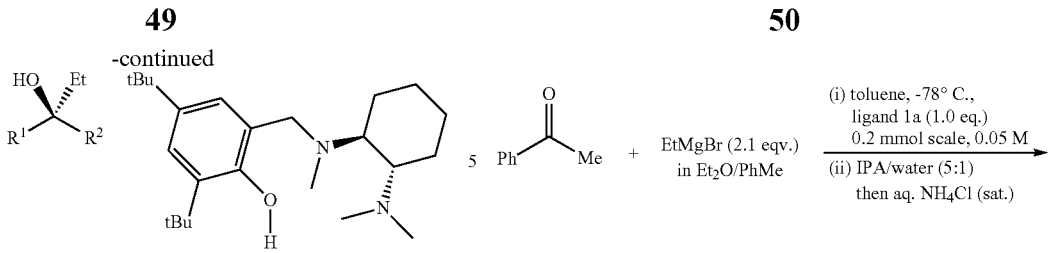

The enantioselectivity and yield obtained for each product is shown below in Table 3.

TABLE 3

| First reactant | Product | Yield (%)[a] | ee [%][b] |
|---|---|---|---|
| (cinnamyl phenyl ketone) | (HO, Et product with phenyl and acetyl) | 57 | 8 |
| | (HO, Et product with styryl) | 43 | 70 |

[a] measured by chiral phase HPLC
[b] measured by chiral phase HPLC

From Examples 4, 5 and 6 it can be seen that the ligand of formula (1) is effective for a range of ketone substrates (including α,β-unsaturated ketones) and a range of Grignard reagents. This ligand also gives moderate to excellent yields of up to 99% and enantioselectivities of tertiary chiral alcohol products of up to 94% ee.

Example 7—Effect of Substituents on a Phenyl Rf Group

The effect of the substituents on the Rf group when Rf is phenyl was then investigated.

Taking acetophenone as the first prochiral reagent, and ethyl magnesium bromide as the Grignard reagent, the ligand of formula (1a) was varied by changing the substituents at positions Y, Ri and Riii on Rf. The ligand having the general formula:

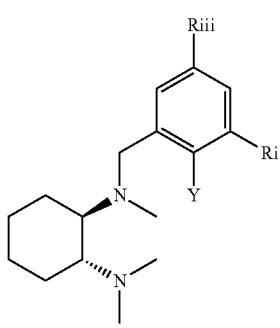

The substituents Y, Ri and Riii were varied as shown below in Table 4, and a series of chiral alcohols were prepared according to the following reaction scheme:

$$\text{Ph-CO-Me} + \text{EtMgBr (2.1 eqv.) in Et}_2\text{O/PhMe} \xrightarrow[\text{(ii) IPA/water (5:1) then aq. NH}_4\text{Cl (sat.)}]{\text{(i) toluene, -78° C., ligand 1a (1.0 eq.) 0.2 mmol scale, 0.05 M}} \text{HO-C(Et)(R}^1\text{)(R}^2\text{)}$$

The enantioselectivities obtained are shown in Table 4 below.

TABLE 4

| Y | Ri | Riii | ee [%][a] |
|---|---|---|---|
| OH | tBu | tBu | 78 |
| OH | tBu | H | 6 |
| OH | H | tBu | 20 |
| OH | H | H | 9 |
| OMe | tBu | tBu | 0 |
| OH | OMe | H | 4 |
| OH | tBu | Br | 72 |
| OH | Cl | Cl | 23 |
| OH | H | tBu | 56 |
| OH | tBu | NMe₂ | 72 |
| OH | tBu | NO₂ | 22 |
| OH | CF₃ | H | 87 |

[a] measured by chiral phase HPLC

It can be seen from Table 4 that the substituent pattern on the phenyl group for Rf can have an effect on the enantioselectivity obtained. It can also be seen, however, that a wide range of substituents at the ortho and para positions (relative to the Y group) give rise to moderate to high enantioselectivities. In particular, an enantioselectivity of 72% was obtained when Ri=t-butyl and Riii=either bromine or N,N-dimethylamine, and an enantioselectivity of 87% was obtained when Ri=trifluoromethyl and Riii=hydrogen. This latter compound is also referred to herein as the chiral ligand of formula (1b).

Example 8—Effect of First Reactant on Stereoselectivity and Yield Using Ligand (1b)

The effect of the first reactant on stereoselectivity and yield was investigated using ligand (1b). The method can be represented generally by the following reaction scheme:

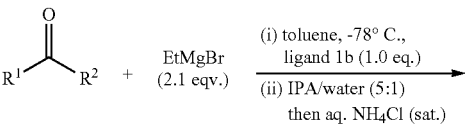

-continued

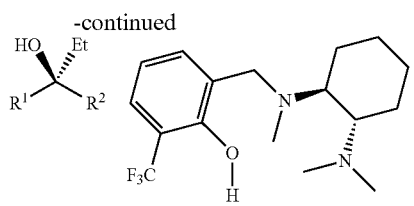

The results are shown in Table 5 below.

TABLE 5

| Product | Yield (%)[a] | ee [%][b] |
|---|---|---|
| (structure 1) | 69 | 87 |
| (structure 2, MeO-phenyl) | 84 | 68 |
| (structure 3, indanyl) | — | 90 |

[a] measured by chiral phase HPLC
[b] measured by chiral phase HPLC

Further studies were also carried out with propiophenone as the first prochiral reagent, methyl magnesium bromide as the Grignard reagent and ligand (1b) under the conditions represented by the reaction scheme above. This resulted in an enantiomeric excess of 92% and a yield of 65% (both measured by chiral phase HPLC.

Like the ligand (1a), the ligand (1b) was found to transmit stereochemical information for alkyl-alkyl and alkyl-aryl ketones with enantiomeric excess values of 84% and above. Unexpectedly high enantiomeric excess values of 90% and above were obtained for the reaction of propiphenone and methyl magnesium bromide (92%) as well as indanone and ethyl magnesium bromide (90%). Ligand (1b) is therefore a particularly advantageous ligand for the process of the present invention.

Example 9—Solvent Studies

To determine the effect of the solvent on the enantioselectivity, studies were carried out in which the solvent was varied in the following reaction scheme:

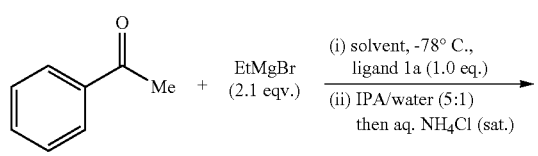

-continued

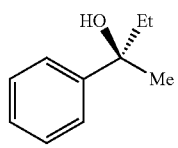

The solvent was varied as shown below in Table 6.

TABLE 6

| Entry | Solvent | Yield [%] | ee[%] |
|---|---|---|---|
| 1 | toluene | 76 | 78 |
| 2 | THF | 86 | 0 |
| 3 | 2-methyl THF | Many products | −17% |
| 4 | 2,5-dimethyl THF | 52 | 73 |
| 5 | MTBE | 84 | 78 |
| 6 | diethyl ether | 46 | 52 |

It can be seen from Table 6 that both non-coordinating solvents such as toluene and ethereal solvents such as MTBE provide reasonable yields and moderate to high enantiomeric excess values. For example, toluene resulted in a yield of 76% and an ee of 78%, and MTBE resulted in a yield of 84% and an ee of 78%.

Importantly, however, the use of THF is not suitable for the process of the invention. It can be seen from Table 6 that THF solvent resulted in an enantiomeric excess of 0%. The use of 2-methyl THF is also not suitable since many products are obtained and the enantiomeric excess is −17% (i.e. 17% of the other enantiomer—here the R enantiomer).

Example 10—Effect of the Addition of TEMPO

To determine the effect of adding TEMPO to the process, studies were carried out according to the following reaction schemes:

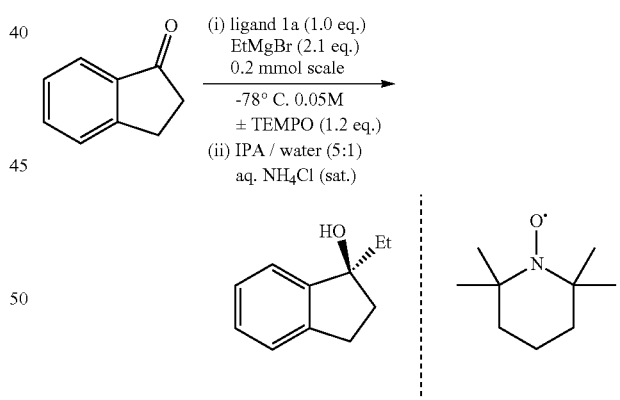

90% ee / 80% yield without TEMPO
97% ee / 52% yield with TEMPO

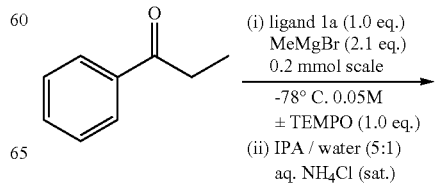

-continued

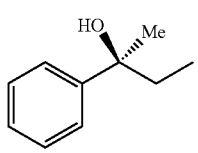

88% ee / 75% yield without TEMPO
91% ee / 61% yield with TEMPO

It can be seen that for both reaction schemes, the enantioselectivity increased with TEMPO but the yield decreased. The yields obtained were, however, still reasonable. These results thus show that the addition of TEMPO can be advantageous for the process of the present invention.

Studies were also carried out in which the amount of TEMPO added was varied. The studies were carried out according to the following reaction scheme:

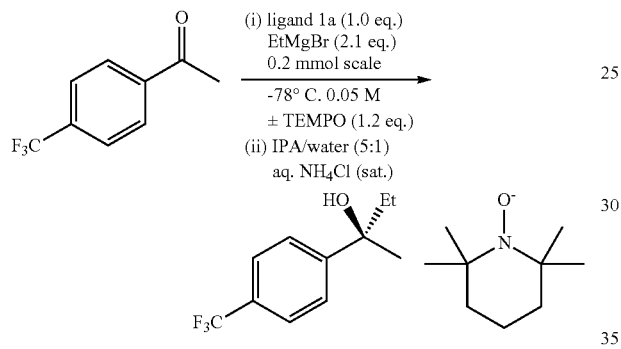

The results obtained with varying amounts of TEMPO are set out below in Table 7.

TABLE 7

| Entry | Additives | Yield [%] | ee[%] |
|---|---|---|---|
| 1 | no additives | 99 | 40 |
| 2 | 0.2 eq. of TEMPO | 99 | 46 |
| 3 | 0.5 eq. of TEMPO | 99 | 48 |
| 4 | 1.0 eq. of TEMPO | 99 | 49 |

It can be seen from Table 7 that the increased addition of TEMPO increased the enantioselectivity from 40% to 49% for the above reaction scheme.

Example 11—Temperature

The reaction of acetophenone and ethylmagnesium bromide was carried out in the presence of the ligand (1a) at −20° C. and resulted in an enantiomeric excess of 64% and a yield of 49% (both measured by chiral HPLC). The reaction can be represented by the following reaction scheme, except the reaction temperature was −20° C.:

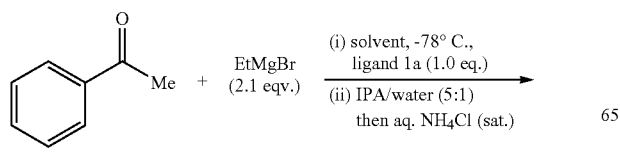

-continued

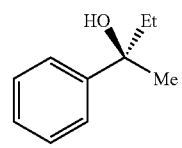

The present invention therefore provides unprecedented asymmetric 1,2-addition of a Grignard reagent to an electrophilic carbon (such as in a carbonyl group of a ketone). This is achieved by the presence of a chiral trans-diamine of formula (1).

The invention claimed is:

1. A process for the stereoselective preparation of a chiral alcohol or a chiral amine, the process comprising:
reacting a first prochiral reactant selected from the group consisting of a ketone, an aldehyde and an imine, with a second reactant comprising a Grignard reagent, in the presence of a chiral trans-diamine of formula (1):

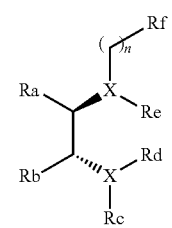

wherein:
X is N;
Ra, Rb, Rc, Rd, and Re are each independently hydrogen, alkyl, aryl, alkenyl, cycloalkyl or cycloalkenyl; or
Ra and Rb may together define a cycloalkyl or cycloalkenyl group; or
Rd and Re may together with the two X atoms define a heterocycloalkyl, heterocycloalkenyl or heteroaryl group;
Rf has the formula:

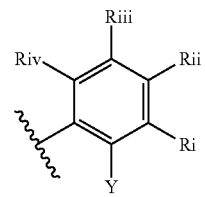

wherein
Y is a hydroxy, amino or aminoalkyl group;
Ri is selected from the group consisting of hydrogen, alkyl, alkenyl, alkynyl, aryl, cycloalkyl, silyl, halo, aminoalkyl, amino, alkoxy, cyano, nitro, heterocyclyl, sulfanyl, phosphanyl and trifluoromethyl; and
Rii, Riii and Riv are each independently selected from the group consisting of hydrogen, alkyl, alkenyl, alkynyl, aryl, cycloalkyl, silyl, halo, aminoalkyl, amino, alkoxy, cyano, nitro, heterocyclyl, sulfanyl, phosphanyl and trifluoromethyl; and
n is an integer in the range of 0 to 3;

wherein the alkyl, aryl, alkenyl, cycloalkyl, cycloalkenyl, heteroaryl, heterocycloalkenyl or heterocycloalkyl groups are optionally substituted.

2. The process according to claim 1, wherein the ketone, aldehyde or imine is formed in-situ.

3. The process according to claim 1,
wherein Ra and Rb together define a $C_3$-$C_7$ cycloalkyl group; or
wherein Ra and Rb are each independently an alkyl or an aryl group.

4. The process according to claim 1, wherein independently one or more of Rc, Rd or Re are a $C_{1-6}$ alkyl group; or wherein Rd and Re together define an imidazole ring with the two N atoms, and optionally Rc is a $C_{1-6}$ alkyl group.

5. The process according to claim 1, wherein n is 1 and/or Rii and Riv are both hydrogen and/or Y is a hydroxy group.

6. The process according to claim 1, wherein Rf is phenol, aniline, N-methylaniline or dimethylaniline, each of which may be optionally substituted by one or more alkyl, alkoxy, cycloalkyl, halo, nitro, aminoalkyl or trifluoromethyl groups.

7. The process according to claim 1, wherein Ri is selected from the group consisting of alkyl, alkoxy, cycloalkyl, halo, or trifluoromethyl, Rii and Riv are both hydrogen and Riii is selected from the group consisting of hydrogen, alkyl, alkoxy, halo, nitro or aminoalkyl.

8. The process according to claim 7, wherein Ri is selected from the group consisting of methyl, tert-butyl, trifluoromethyl, adamantyl, and methoxy, and Riii is selected from the group consisting of hydrogen, methyl, tert-butyl, halo, N,N-dimethylamine and methoxy.

9. The process according to claim 1, wherein Rf has the formula:

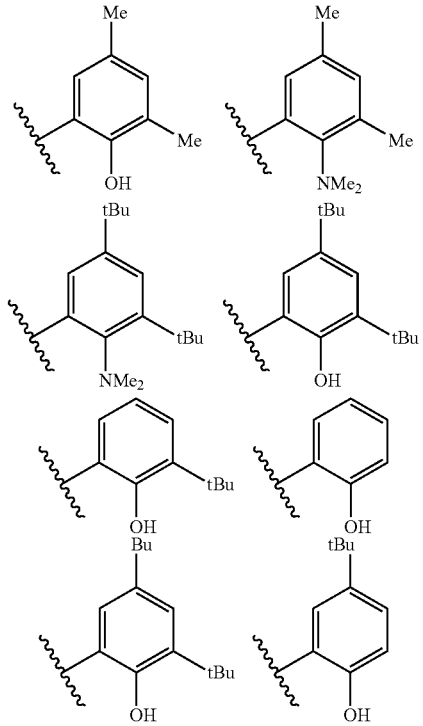

10. The process according to claim 9, wherein Rf has the formula:

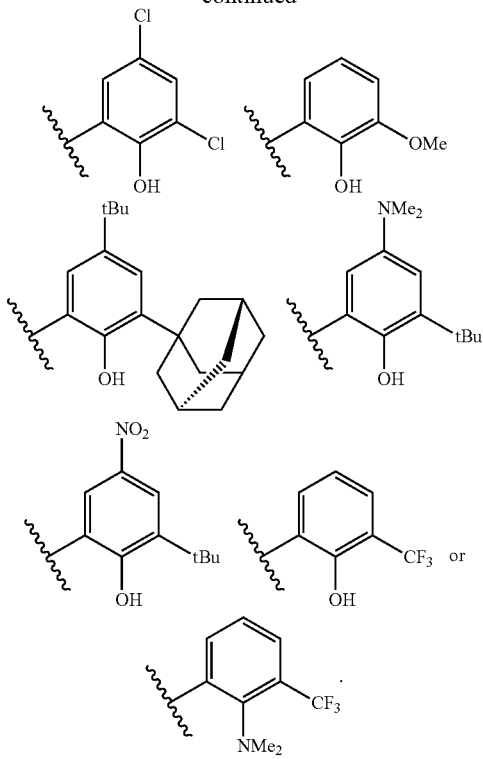

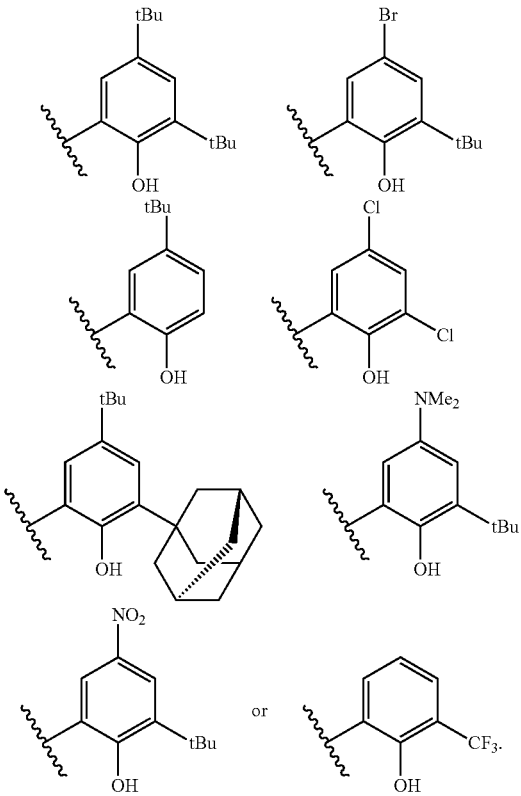

11. The process according to claim 9, wherein Rf has the formula:
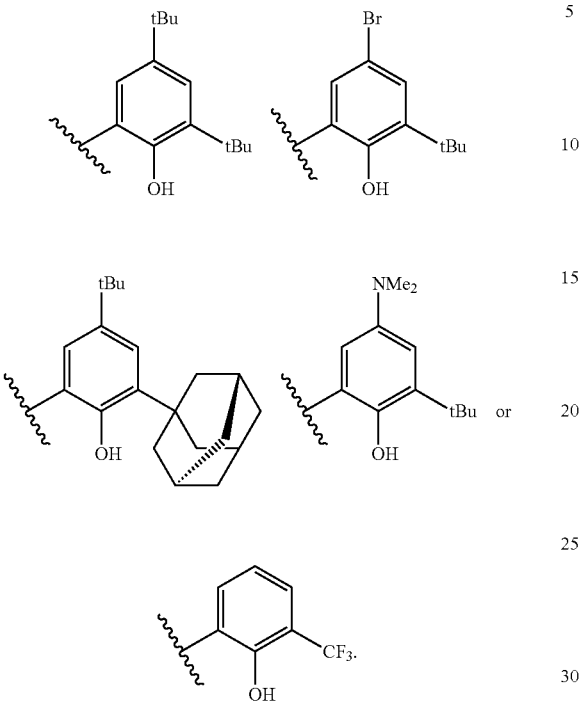
12. The process according to claim 9, wherein Rf has the formula
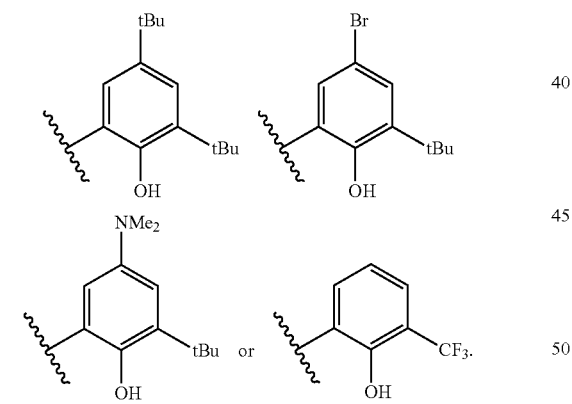
13. The process according to claim 9, wherein Rf has the formula:
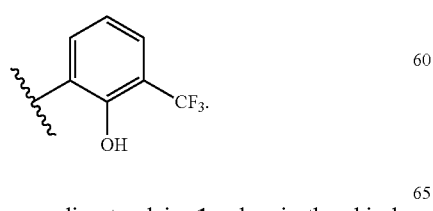
14. The process according to claim 1, wherein the chiral trans-diamine has the formula:
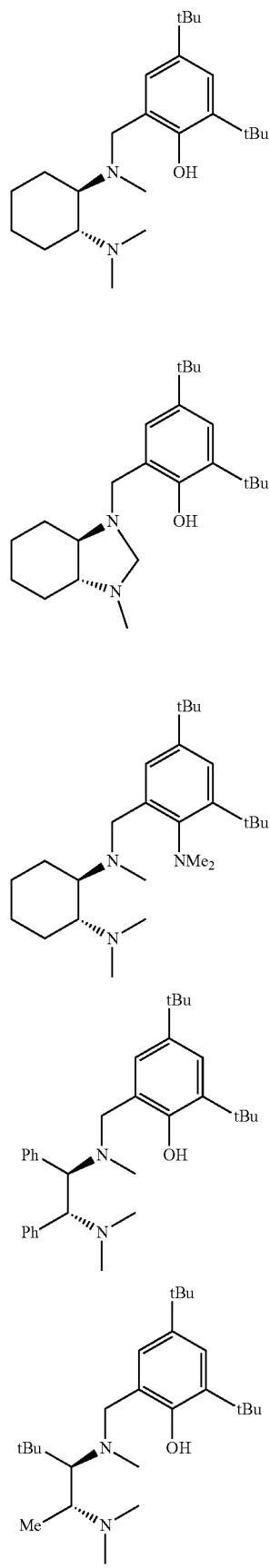

-continued
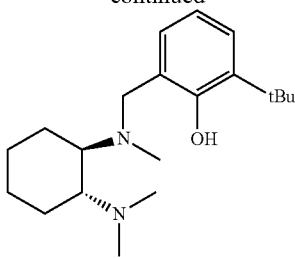
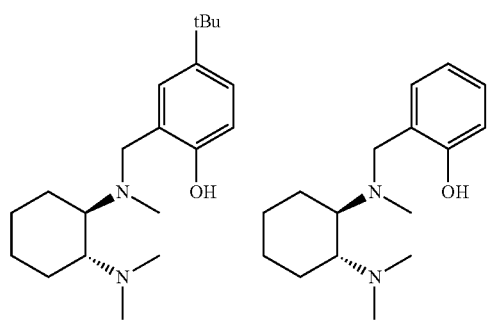
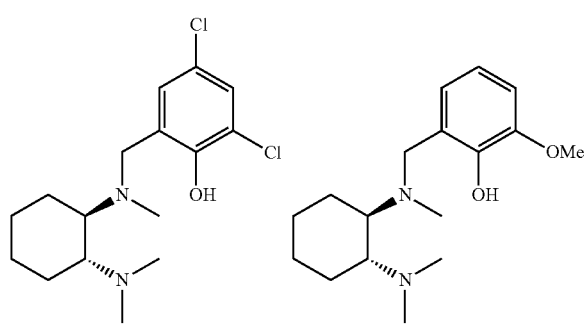
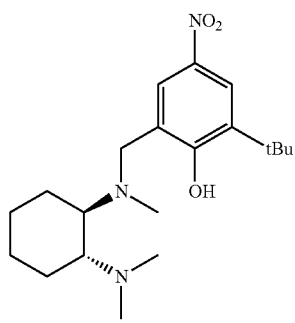
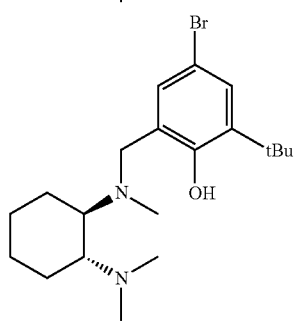
-continued
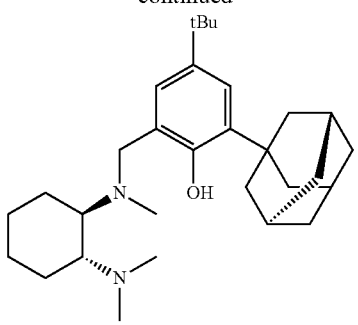
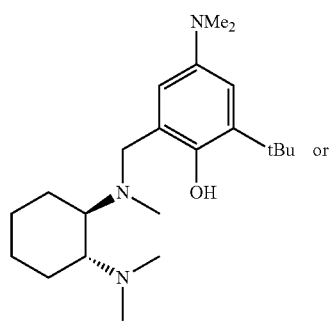
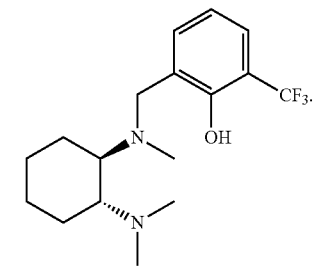
15. The process according to claim 14, wherein the chiral trans-diamine has the formula:
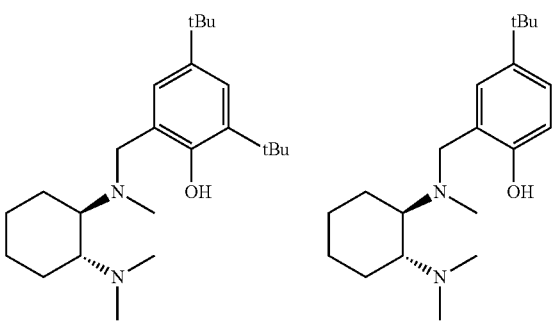
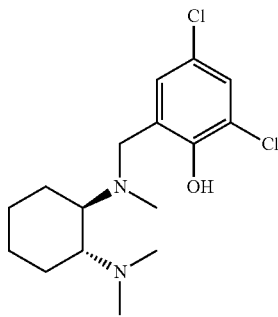

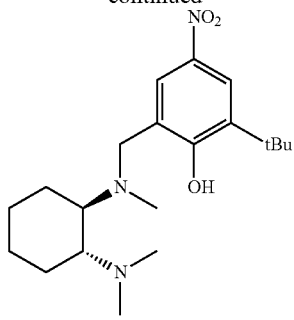
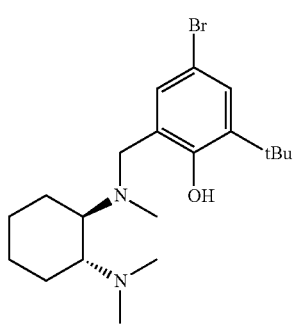
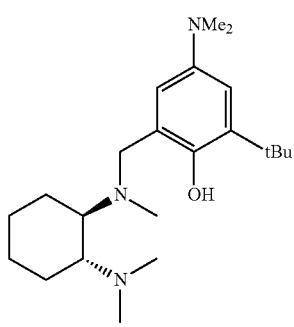
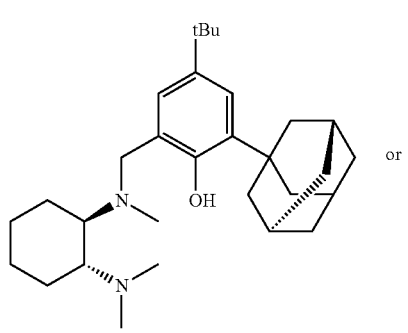 or
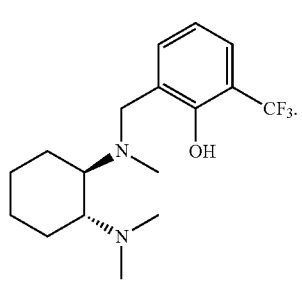
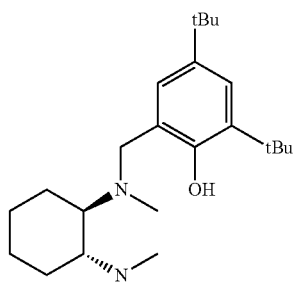
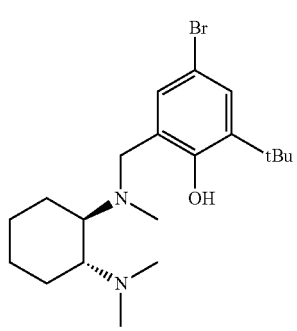
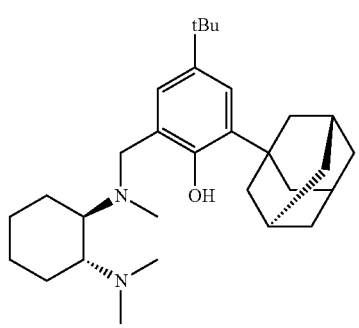
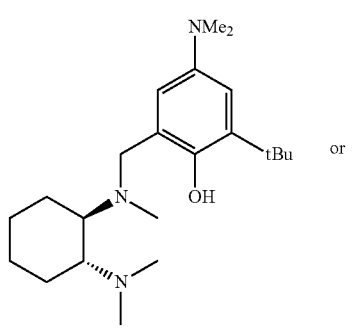 or
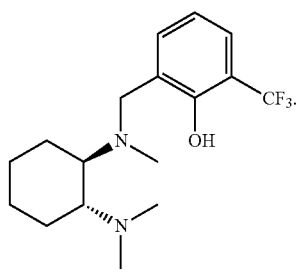
16. The process according to claim 14, wherein the chiral trans-diamine has the formula:
17. The process according to claim 16, wherein the chiral trans-diamine has the formula:

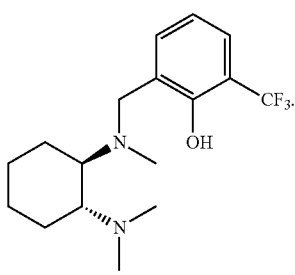 [SMILES: CN(C)[C@@H]1CCCC[C@H]1N(C)Cc1cccc(C(F)(F)F)c1O]

18. The process according to claim 1, wherein said process is performed in the presence of a non-coordinating solvent such as toluene, pentane, benzene, cyclopentane, heptane, xylene, hexane, 1,2-difluorobenzene, dichloromethane or an ethereal solvent which is not tetrahydrofuran or 2-methyl tetrahydrofuran and/or in the presence of TEMPO.

19. The process according to claim 1, wherein
   (i) the ketone is of the formula:

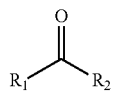

wherein:
   $R_1$ and $R_2$ are each independently alkyl, aryl, alkenyl, cycloalkyl or cycloalkenyl; or
   $R_1$ and $R_2$ together define a cycloalkyl, cycloalkenyl, heterocycloalkyl or heterocycloalkenyl group;

(ii) the aldehyde is of the formula:

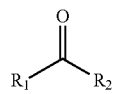

wherein:
   $R_1$ and $R_2$ are each independently hydrogen, alkyl, aryl, alkenyl, cycloalkyl or cycloalkenyl, provided that at least one of $R_1$ and $R_2$ is hydrogen; or
   (iii) the imine is of the formula:

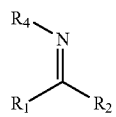

wherein:
   $R_1$ and $R_2$ are each independently hydrogen, alkyl, aryl, alkenyl, cycloalkyl or cycloalkenyl; or
   $R_1$ and $R_2$ together define a cycloalkyl, cycloalkenyl, heterocycloalkyl or heterocycloalkenyl group.

20. The process according to claim 19, wherein $R_1$ and $R_2$ in the aldehyde are not both hydrogen and wherein $R_1$ and $R_2$ in the imine are not both hydrogen.

21. The process according to claim 1, wherein the Grignard reagent is of the formula $R_3$—MgX, wherein $R_3$ is an aryl, cycloalkyl, alkyl, alkenyl or alkynyl group, each of which may be optionally substituted and wherein X is a halogen.

22. The process of claim 1, wherein Ra and Rb together is cyclohexane or cyclopentane.

23. The process of claim 1, wherein Ra and Rb are each independently selected from the group consisting of phenyl, methyl and tert-butyl.

* * * * *